(12) United States Patent
Staehle et al.

(10) Patent No.: US 8,841,324 B2
(45) Date of Patent: Sep. 23, 2014

(54) HETEROCYCLIC COMPOUNDS AS AUTOTAXIN INHIBITORS

(75) Inventors: Wolfgang Staehle, Ingelheim (DE); Kai Schiemann, Seeheim-Jugenheim (DE); Melanie Schultz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 300 days.

(21) Appl. No.: 13/259,464

(22) PCT Filed: Mar. 3, 2010

(86) PCT No.: PCT/EP2010/001324
§ 371 (c)(1), (2), (4) Date: Sep. 23, 2011

(87) PCT Pub. No.: WO2014/112116
PCT Pub. Date: Oct. 7, 2010

(65) Prior Publication Data
US 2012/0015959 A1    Jan. 19, 2012

(30) Foreign Application Priority Data
Apr. 2, 2009 (EP) .................................... 09004858

(51) Int. Cl.
| | |
|---|---|
| *A01N 43/40* | (2006.01) |
| *A61K 31/445* | (2006.01) |
| *A01N 43/38* | (2006.01) |
| *A61K 31/40* | (2006.01) |
| *A61K 31/405* | (2006.01) |
| *A01N 43/52* | (2006.01) |
| *A61K 31/415* | (2006.01) |
| *C07D 403/00* | (2006.01) |
| *C07D 211/32* | (2006.01) |
| *C07D 249/18* | (2006.01) |
| *C07D 403/12* | (2006.01) |
| *C07D 401/12* | (2006.01) |
| *C07D 209/08* | (2006.01) |
| *C07D 413/12* | (2006.01) |
| *C07D 231/56* | (2006.01) |
| *C07D 413/06* | (2006.01) |
| *C07D 263/58* | (2006.01) |

(52) U.S. Cl.
CPC ............ *C07D 249/18* (2013.01); *C07D 403/12* (2013.01); *C07D 401/12* (2013.01); *C07D 209/08* (2013.01); *C07D 413/12* (2013.01); *C07D 231/56* (2013.01); *C07D 413/06* (2013.01); *C07D 263/58* (2013.01)
USPC ........... 514/322; 514/414; 514/415; 514/394; 544/366; 544/373; 546/199; 546/220

(58) Field of Classification Search
USPC .......... 514/322, 414, 415, 394; 544/366, 373; 546/199, 220
See application file for complete search history.

(56) References Cited

FOREIGN PATENT DOCUMENTS
| | | |
|---|---|---|
| WO | WO 02/30422 A1 | 4/2002 |
| WO | WO 02/080928 A1 | 10/2002 |
| WO | WO 2009/046841 A2 | 4/2009 |

OTHER PUBLICATIONS

JP 2001139574, 2001, pp. 1-2.*
International Search Report of PCT/EP2010/001324 (Apr. 21, 2010).
A. L. Parrill et al., "Virtual Screening Approaches for the Identification of Non-Lipid Autotaxin Inhibitors", Bioorganic & Medicinal Chemistry, vol. 16, No. 4 (Feb. 2008) pp. 1784-1795.

* cited by examiner

*Primary Examiner* — Samira Jean-Louis
(74) *Attorney, Agent, or Firm* — Millen, White, Zelano & Branigan, P.C.

(57) ABSTRACT

Compounds of the formula (I), in which Het, R, X, Y, $R^1$ and p have the meanings indicated in claim 1, are autotaxin inhibitors and can be employed for the treatment of tumors.

20 Claims, No Drawings

HETEROCYCLIC COMPOUNDS AS AUTOTAXIN INHIBITORS

BACKGROUND OF THE INVENTION

The invention was based on the object of finding novel compounds having valuable properties, in particular those which can be used for the preparation of medicaments.

The present invention relates to compounds and to the use of compounds for the treatment of diseases which are accompanied by an increase in the lysophosphatidic acid level, furthermore to pharmaceutical compositions which comprise these compounds.

In detail, the present invention relates to compounds of the formula I, which preferably inhibit one or more enzymes which regulate and/or modulate the lysophosphatidic acid (or LPA for short) level, to compositions which comprise these compounds, and to processes for the use thereof for the treatment of diseases and complaints, such as angiogenesis, cancer, tumor formation, growth and propagation, arteriosclerosis, ocular diseases, choroidal neovascularisation and diabetic retinopathy, inflammatory diseases, arthritis, neurodegeneration, restenosis, wound healing or transplant rejection. In particular, the compounds according to the invention are suitable for the therapy or prophylaxis of cancer diseases.

Autotaxin (ATX) is an enzyme which is responsible for the increase in the lysophosphatidic acid level in ascites and plasma (Xu et al. 1995, Clinical Cancer Research Vol. 1, page 1223 and Xu et al. 1995, Biochem. J. Vol-309, page 933). ATX converts lysophatidylcholine (LPC) into lysophosphatidic acid (Tokumura et al. 2002, J. Biol. Chem., Vol 277, page 39436 and Umezu-Gozo et al. 2002, J. Biol. Chem., Vol. 158, page 227) LPA is an intercellular lipid mediator which influences a multiplicity of biological and biochemical processes, such as, for example, smooth muscle contraction, thrombocyte aggregation and apoptosis (Tigyi et al. 2003 Prog. Lipid Res. Vol 42, page. 498 and Mills et al. 2003 Nat. Rev. Cancer Vol. 3, page 582 and Lynch et al. 2001 Prost. Lipid Med. Vol. 64, page 33). In addition, LPA can be found in increased concentrations in plasma and ascites fluid from ovarian cancer patients in the early and late phase. LPA plays a role there in tumor cell proliferation and invasion thereof into neighbouring tissue, which can result in metastasisation (Xu et al. 1995, Clinical Cancer Research Vol. 1, page 1223 and Xu et al. 1995, Biochem. J. Vol-309, page 933). These biological and phatobiological processes are switched on by the activation by LPA of G-protein-coupled receptors (Contos et al. 2000, Mol. Pharm. Vol 58, page. 1188).

For this reason, it is desirable to lower the LPA level for the treatment of tumor patients. This can be achieved by the inhibition of enzymes which are involved in LPA biosynthesis, such as, for example, autotaxin (ATX, Sano et al. 2002, J. Biol. Chem. Vol. 277, page 21197 and Aoki et al. 2003, J. Biol. Chem. Vol. 277 page 48737). Autotaxin belongs to the enzyme family of the nucleotides pyrophosphatases and phosphodiesterases (Goding et al. 1998, Immunol. Rev. Vol. 161, page 11) and represents an important starting point in antitumor therapy (Mills et al. 2003 Nat. Rev. Cancer Vol. 3, page 582 and Goto eta I. 2004 J. Cell. Biochem. Vol. 92, page 1115) since it is expressed to an increased extent in tumors and causes tumor cell proliferation and invasion into neighbouring tissue, which can result in metastases formation (Nam et al. 2000, Oncogene, Vol. 19 page 241). In addition, autotaxin together with other angiogenetic factors causes blood vessel formation in the course of angiogenesis (Nam et al. 2001, Cancer Res. Vol. 61 page. 6938). Angiogenesis is an important process in tumor growth, which ensures supply of the tumor with nutrients. For this reason, inhibition of angiogenesis is an important starting point in cancer and tumor therapy, with which the tumor can be starved to a certain extent (Folkman, 2007, Nature Reviews Drug Discovery Vol. 6, page 273-286).

Surprisingly, it has been found that the compounds according to the invention cause specific inhibition of the enzyme family of the nucleotides pyrophosphatases and phosphodiesterases, in particular autotaxin. The compounds according to the invention preferably exhibit an advantageous biological activity, which can easily be detected in the test described, for example, herein. In tests of this type, the compounds according to the invention preferably exhibit and cause an inhibiting effect, which is usually documented by $IC_{50}$ values in a suitable range, preferably in the micromolar range and more preferably in the nanomolar range.

In general, all solid and non-solid tumors can be treated with the compounds of the formula I, such as, for example, monocytic leukaemia, brain, urogenital, lymphatic system, stomach, laryngeal, ovarian and lung carcinoma, including lung adenocarcinoma and small-cell lung carcinoma. Further examples include prostate, pancreatic and breast carcinoma.

As discussed herein, effects of the compound according to the invention are relevant for various diseases. Accordingly, the compounds according to the invention are useful in the prophylaxis and/or treatment of diseases which are influenced by inhibition of one or more nucleotides pyrophosphatases and/or phosphodiesterases, in particular autotaxin.

The present invention therefore relates to compounds according to the invention as medicaments and/or medicament active ingredients in the treatment and/or prophylaxis of the said diseases and to the use of compounds according to the invention for the preparation of a pharmaceutical agent for the treatment and/or prophylaxis of the said diseases, and also to a method for the treatment of the said diseases comprising the administration of one or more compounds according to the invention to a patient in need of such administration.

It can be shown that the compounds according to the invention have an advantageous action in a xenotransplant tumor model.

The host or patient can belong to any mammalian species, for example a primate species, in particular humans; rodents, including mice, rats and hamsters; rabbits; horses, cattle, dogs, cats, etc. Animal models are of interest for experimental investigations, where they provide a model for the treatment of a human disease.

The sensitivity of a certain cell to treatment with the compounds according to the invention can be determined by testing in vitro. Typically, a culture of the cell is combined with a compound according to the invention at various concentrations for a time which is sufficient to enable the active agents to induce cell death or to inhibit cell migration or to block the cellular secretion of angiogenesis-promoting substances, usually between approximately one hour and one week. For testing in vitro, cultivated cells from a biopsy sample can be used. The viable cells remaining after the treatment are then counted.

The dose varies depending on the specific compound used, the specific disease, the patient status, etc. Typically, a therapeutic dose is sufficient to considerably reduce the undesired cell population in the target tissue, while the viability of the patient is maintained. The treatment is generally continued until a considerable reduction has occurred, for example at least about a 50% reduction in the cell burden, and can be continued until essentially no undesired cells can be detected in the body.

PRIOR ART

Compounds which are capable of inhibiting autotaxin are described in Peng et al. Bioorganic & Medicinal Chemistry Letters (17, 2007, page 1634-1640). The compounds described therein are lipid analogues, which do not have any structural features in common with the compounds according to the invention.

SUMMARY OF THE INVENTION

The invention relates to compounds of the formula I

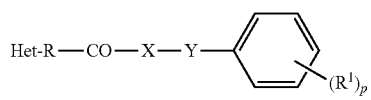

in which
R$^1$ denotes H, A, Hal, OR$^3$, N(R$^3$)$_2$, N=CR$^3$N(R$^3$)$_2$, SR$^3$, NO$_2$, CN, COOR$^3$, CON(R$^3$)$_2$, NR$^3$COA, NR$^3$SO$_2$A, SO$_2$N(R$^3$)$_2$, S(O)$_m$A, —[C(R$^3$)$_2$]$_n$N(R$^3$)$_2$, O[C(R$^3$)$_2$]$_p$N(R$^3$)$_2$, S[C(R$^3$)$_2$]$_n$N(R$^3$)$_2$, —NR$^3$[C(R$^3$)$_2$]$_n$N(R$^3$)$_2$, NHCON(R$^3$)$_2$, CON(R$^3$)$_2$, CONR$^3$[C(R$^3$)$_2$]$_n$N(R$^3$)$_2$ or COA,
R$^3$ denotes H or A,
X denotes O, NH or CH$_2$,
Y denotes CH$_2$, CH$_2$O or is absent,
R denotes

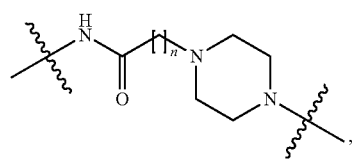

n = 2 or 3

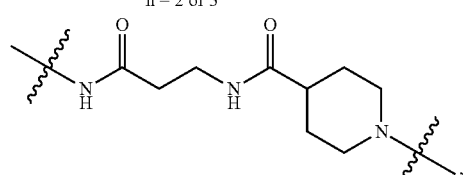

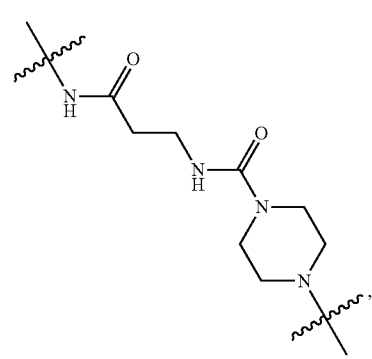

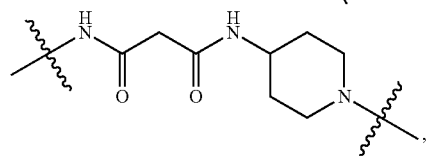

-continued

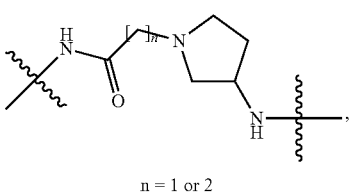

n = 1 or 2

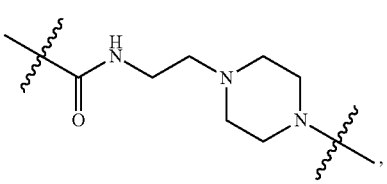

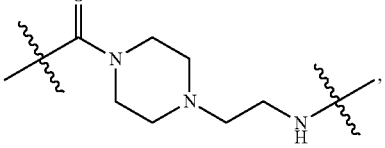

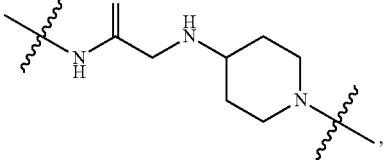

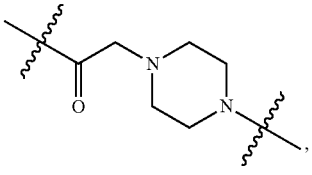

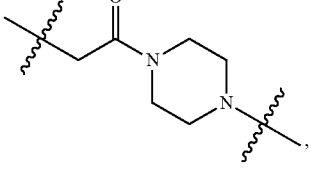

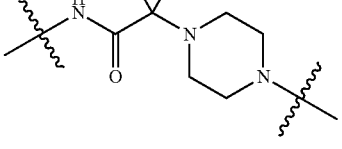

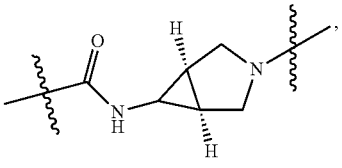

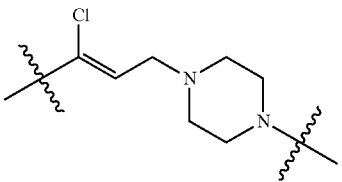

-continued

[Structure: F,F-difluoro group with propyl-piperazine linker]

[Structure: pyrazoline with ethyl-piperazine linker]

[Structure: HO-CH with propyl-piperazine linker] or

[Structure: CH-OH with methyl-piperazine linker]

R⁴ denotes H, A or phenyl,
Het denotes

[Structures: benzotriazole, benzimidazole, benzoxazolone, indazole, indole, or benzothiazolone]

A denotes unbranched or branched alkyl having 1-10 C atoms, in which 1-7H atoms may be replaced by OH, F, Cl and/or Br, and/or in which one or two CH$_2$ groups may be replaced by O, NH and/or S,
or
cyclic alkyl having 3-7 C atoms,
Hal denotes F, Cl, Br or I,
n denotes 0, 1, 2 or 3,
m denotes 0, 1 or 2,
p denotes 0, 1, 2, 3, 4 or 5,
and pharmaceutically usable salts and stereoisomers thereof, including mixtures thereof in all ratios.

Compounds of the formula I also mean pharmaceutically usable derivatives thereof, optically active forms (stereoisomers), tautomers, polymorphs, enantiomers, racemates, diastereomers and the hydrates and solvates of these compounds. The term solvates of the compounds is taken to mean adductions of inert solvent molecules onto the compounds which form owing to their mutual attractive force. solvates are, for example, mono- or dihydrates or alcoholates.

Pharmaceutically usable derivatives are taken to mean, for example, the salts of the compounds according to the invention and also so-called prodrug compounds.

Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to the patent claims and pharmaceutically usable salts, and stereoisomers thereof, characterised in that a) for the preparation of compounds of the formula I in which R denotes

[Structure: -NH-C(=O)-CH$_2$-NH-piperidine-N-]

a compound of the formula II

Het-NH—CO—CH$_2$-L  II in which
Het has the meaning indicated in claim 1,
and L denotes Cl or Br,
is reacted with a compound of the formula III

[Structure: H$_2$N-piperidine-N-CO-X-Y-phenyl(R¹)$_p$]  III in which
X, Y, R¹ and p have the meanings indicated in claim 1, or
b) for the preparation of compounds of the formula I in which R denotes

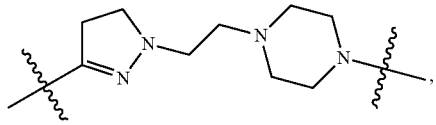 [SMILES: *C1=NN(CCN2CCN(*)CC2)CC1], a compound of the formula IV

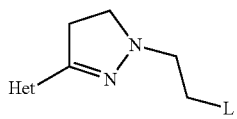

in which
Het has the meaning indicated in claim 1,
and L denotes Cl or Br,
is reacted with a compound of the formula V

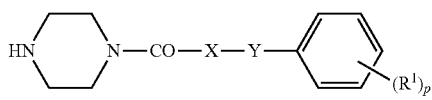

in which
X, Y, R$^1$ and p have the meanings indicated in claim 1,
or
c) for the preparation of compounds of the formula I in which R denotes

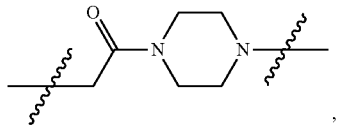 [SMILES: *CC(=O)N1CCN(*)CC1], a compound of the formula VI

Het-CH$_2$—CO-L  VI in which
Het has the meaning indicated in claim 1,
and L denotes Cl, Br, I or a free or reactively functionally modified OH group,
is reacted with a compound of the formula V,
or
d) for the preparation of compounds of the formula I in which R denotes

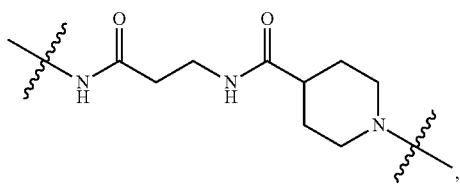 [SMILES: *NC(=O)CCNC(=O)C1CCN(*)CC1], a compound of the formula VII

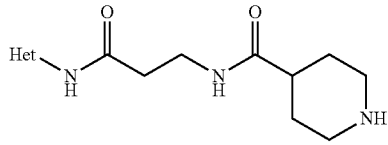

in which
Het has the meaning indicated in claim 1,
is reacted with a compound of the formula VIII

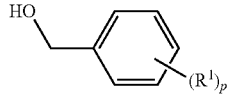

in which
R$^1$ and p have the meanings indicated in claim 1,
and a compound selected from the group carbonyldiimidazole, phosgene, diphosgene, triphosgene,
or
e) for the preparation of compounds of the formula I in which R denotes

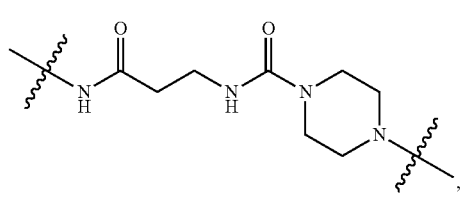 [SMILES: *NC(=O)CCNC(=O)N1CCN(*)CC1], a compound of the formula IX

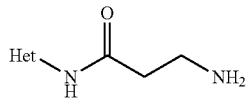

in which
Het has the meaning indicated in claim 1,
is reacted with a compound of the formula V
and a compound selected from the group carbonyldiimidazole, phosgene, diphosgene, triphosgene,
or
f) for the preparation of compounds of the formula I in which R denotes

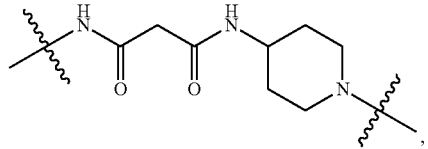 [SMILES: *NC(=O)CC(=O)NC1CCN(*)CC1], a compound of the formula X

Het-NH$_2$   X

IV

V

VI

VII

VIII

IX in which
Het has the meaning indication in Claim 1,
is reacted with a compound of the formula XI

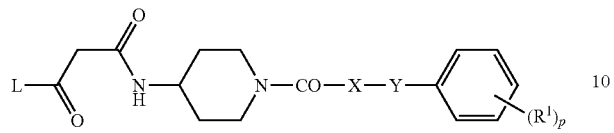

XI in which
X, Y, R¹, p have the meanings indicated in claim 1,
and L denotes Cl, Br, I or a free or reactively functionally modified OH group,
and/or a base or acid of the formula I is converted into one of its salts.

A denotes alkyl and is preferably unbranched (linear) or branched, and has 1, 2, 3, 4, 5, 6, 7, 8, 9 or 10 C atoms. Alkyl preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

Alkyl very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. Alkyl also denotes cycloalkyl.

Cycloalkyl preferably denotes cyclopropyl, cyclobutyl, cyclopentyl, cyclohexyl or cycloheptyl.

Hal preferably denotes F, Cl or Br, but also I, particularly preferably Br or Cl.

R¹ preferably denotes Hal.
R³ preferably denotes H or methyl.
X preferably denotes 0 the CH₂.
Y preferably denotes CH₂ or CH₂O.
p preferably denotes 1, 2 or 3, furthermore 4 or 5.
n preferably denotes 0, 1, 2 or 3.

Throughout the invention, all radicals which occur more than once, such as, for example, R, may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above.

Some preferred groups of compounds may be expressed by the following sub-formulae Ia to Ie, which conform to the formula I and in which the radicals not designated in greater detail have the meaning indicated for the formula I, but in which
in Ia R¹ denotes Hal;
in Ib X denotes O or CH₂;
in Ic Y denotes CH₂ or CH₂O;
in Id p denotes 1, 2 or 3;
in Ie R¹ denotes Hal,
  X denotes O or CH₂,
  Y denotes CH₂ or CH₂O, R denotes

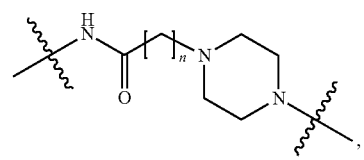

n = 2 or 3

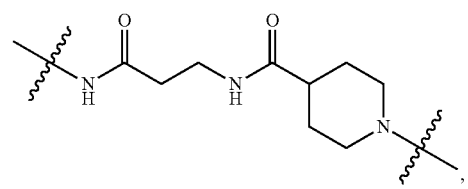

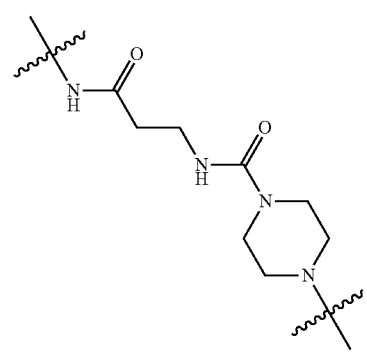

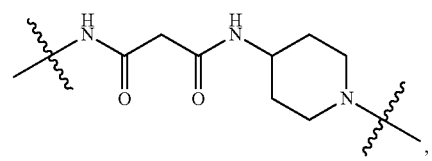

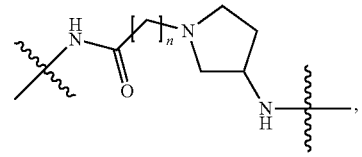

n = 1 or 2

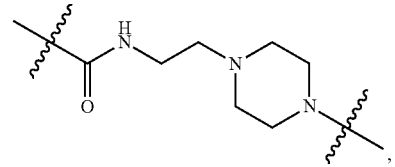

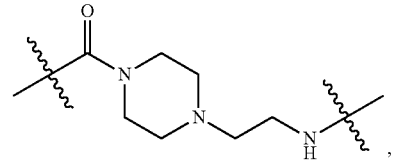

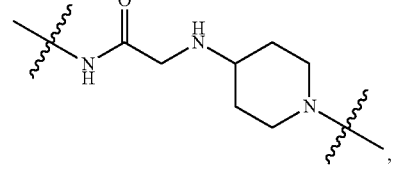

-continued

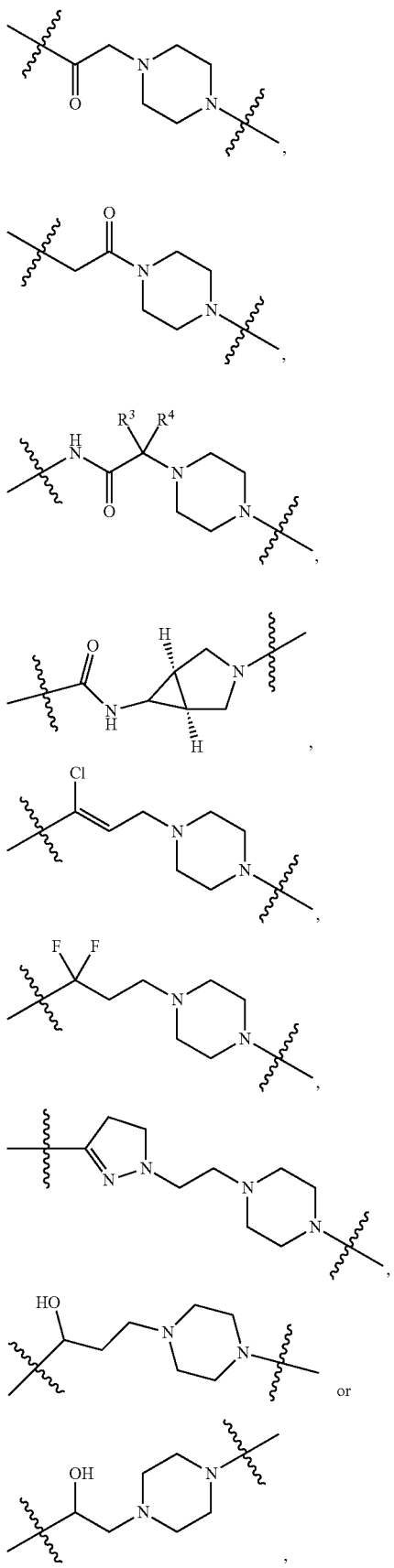

Het denotes

A denotes unbranched or branched alkyl having 1-10 C atoms, in which 1-7H atoms may be replaced F and/or Cl, Hal denotes F, Cl, Br or I, p denotes 1, 2 or 3, and pharmaceutically usable salts and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting materials can, if desired, also be formed in situ by not isolating them from the reaction mixture, but instead immediately converting them further into the compounds of the formula I.

The starting compounds of the formulae II, III, IV, V, VI, VII, VIII, IX, X and XI are generally known. If they are novel, however, they can be prepared by methods known per se.

The starting materials are generally also commercially available.

In the compounds of the formula II, IV, VI, XI, L preferably denotes Cl, Br, I or a free or a reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Compounds of the formula I can preferably be obtained by reacting a compound of the formula II with a compound of the formula III.

The reaction is generally carried out in an inert solvent, in the presence of an acid-binding agent preferably an alkali or alkaline-earth metal hydroxide, carbonate or bicarbonate or another salt of a weak acid of the alkali or alkaline-earth metals, preferably of potassium, sodium, calcium or caesium. The addition of an organic base, such as triethylamine, dimethylaniline, pyridine or quinoline, may also be favourable.

Depending on the conditions used, the reaction time is between a few minutes and 14 days, the reaction temperature is between about −30° and 140°, normally between −10° and 90°, in particular between about 0° and about 70°, very particularly preferably between 15 and 35° C.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to pyridine, acetonitrile, dichloromethane and/or DMF.

Compounds of the formula I can furthermore preferably be obtained by reacting a compound of the formula IV with a compound of the formula V under conditions as described above.

The reaction is preferably carried out in acetonitrile at 100° C. with addition of $NaHCO_3$.

Compounds of the formula I can furthermore preferably be obtained by reacting a compound of the formula VI with a compound of the formula V. In the compounds of the formula VI, L preferably denotes OH. For the reaction, the carboxyl group is preferably converted into an active ester.

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example by addition of HOBt or N-hydroxysuccinimide.

The reaction preferably succeeds in the presence of a dehydrating agent, such as, for example, a carbodiimide, such as N,N'-dicyclohexylcarbodiimide ("DCCI"), 1,1'-carbonyldiimidazole (CDI) or N-3-dimethylaminopropyl-N'-ethylcarbodiimide ("DAPECI"), furthermore propanephosphonic anhydride (cf. Angew. Chem. 92, 129 (1980)), diphenylphosphoryl azide or 2-ethoxy-N-ethoxycarbonyl-1,2-dihydroquinoline.

The reaction is generally carried out in an inert solvent.

Depending on the conditions used, the reaction time is between a few minutes and 14 days, the reaction temperature is between about −15° and 150°, normally between −5° and 90°, particularly preferably between 20° and 60° C. The reaction is preferably carried out in DMF at room temperature and preferably with addition of N-methylmorpholine.

Compounds of the formula I can furthermore preferably be obtained by reacting a compound of the formula VII with a compound of the formula VIII and a compound selected from the group carbonyldiimidazole, phosgene, diphosgene, triphosgene.

The reaction is carried out in an inert solvent and under conditions as described above. The reaction is preferably carried out in DMF at room temperature and with addition of a carbonyl component, such as CDI.

Compounds of the formula I can furthermore preferably be obtained by reacting a compound of the formula IX with a compound of the formula V and a compound selected from the group carbonyldiimidazole, phosgene, diphosgene, triphosgene.

The reaction is carried out in an inert solvent and under conditions as described above. The reaction is preferably carried out in DMF at room temperature and with addition of a carbonyl component, such as CDI, and a base, such as triethylamine.

Compounds of the formula I can furthermore preferably be obtained by reacting a compound of the formula VX with a compound of the formula XI. The reaction is preferably carried out under conditions like the reaction of the compound of the formula VI with a compound of the formula V.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethane-sulfonate, toluene-sulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalene-sulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner.

The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable salts and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidephenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated;

and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or more usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

The medicaments from Table 1 are preferably, but not exclusively, combined with the compounds of the formula I. A combination of the formula I and medicaments from Table I can also be combined with compounds of the formula VI.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | |
| | Ormiplatin | BBR-3464 (Hoffmann-La Roche) |
| | Iproplatin | |
| | | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma- Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | | BNP-1350 (BioNumerik) |
| | Pixantrone (Novuspharma) | CKD-602 (Chong Kun |

TABLE 1-continued

| | | |
|---|---|---|
| | Rebeccamycin analogue (Exelixis) | Dang) KW-2170 (Kyowa Hakko) |
| | BBR-3576 (Novuspharrna) | |
| Antitumour antibiotics | Dactinomycin (Actinomycin D) | Amonafide Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxorubicin | |
| | Mitoxantron (Novantron) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) ER-86526 (Eisai) |
| | Cemadotin (BASF) | Combretastatin A4 (BMS) |
| | RPR 109881A (Aventis) | Isohomohalichondrin-B |
| | TXD 258 (Aventis) | (PharmaMar) |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | Azaepothilon B (BMS) |
| | BMS 247550 (BMS) | BNP- 7787 (BioNumerik) |
| | BMS 184476 (BMS) | CA-4-Prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) ZD-9331 (BTG) | Nolatrexed (Eximias) CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-Benzylguanine (Paligent) |
| | Thymectacin (NewBiotics) | |
| | Edotreotid (Novartis) | |
| Farnesyl transferase inhibitors | Arglabin (NuOncology Labs) Ionafarnib (Schering-Plough) BAY-43-9006 (Bayer) | Tipifarnib (Johnson & Johnson) Perillyl alcohol (DOR BioPharma) |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) SAHA (Aton Pharma) MS-275 (Schering AG) | Pivaloyloxymethyl butyrate (Titan) Depsipeptide (Fujisawa) |
| Metalloproteinase inhibitors | Neovastat (Aeterna Laboratories) | CMT -3 (CollaGenex) BMS-275291 (Celltech) |
| Ribonucleoside reductase inhibitors | Marimastat (British Biotech) | Tezacitabine (Aventis) Didox (Molecules for Health) |
| | Gallium maltolate (Titan) | |
| | Triapin (Vion) | |
| TNF-alpha agonists/ antagonists | Virulizin (Lorus Therapeutics) CDC-394 (Celgene) | Revimid (Celgene) |
| Endothelin-A receptor antagonists | Atrasentan (Abbot) ZD-4054 (AstraZeneca) | YM-598 (Yamanouchi) |

TABLE 1-continued

| Category | | |
|---|---|---|
| Retinoic acid receptor agonists | Fenretinide (Johnson & Johnson) <br> LGD-1550 (Ligand) | Alitretinoin (Ligand) |
| Immunomodulators | Interferon <br> Oncophage (Antigenics) <br> GMK (Progenies) <br> Adenocarcinoma vaccine (Biomira) <br> CTP-37 (AVI BioPharma) <br> JRX-2 (Immuno-Rx) <br> PEP-005 (Peplin Biotech) <br> Synchrovax vaccines (CTL Immuno) <br> Melanoma vaccine (CTL Immuno) <br> p21-RAS vaccine (GemVax) | Dexosome therapy (Anosys) <br> Pentrix (Australian Cancer Technology) <br> JSF-154 (Tragen) <br> Cancer vaccine (Intercell) <br> Norelin (Biostar) <br> BLP-25 (Biomira) <br> MGV (Progenies) <br> !3-Alethin (Dovetail) <br> CLL-Thera (Vasogen) |
| Hormonal and antihormonal agents | Oestrogens <br> Conjugated oestrogens <br> Ethynyloestradiol <br> chlorotrianisene <br> Idenestrol <br> Hydroxyprogesteroncaproat <br><br> Medroxyprogesterone <br> Testosterone <br> Testosterone propionate <br> Fluoxymesterone <br> Methyltestosterone <br> Diethylstilbestrol <br> Megestrol <br> Tamoxifen <br> Toremofin <br> Dexamethasone | Prednisone <br> Methylprednisolone <br> Prednisolone <br> Aminoglutethimide <br> Leuprolide <br> Goserelin <br> Leuporelin <br> Bicalutamide <br> Flutamide <br> Octreotide <br> Nilutamide <br> Mitotan <br> P-04 (Novogen) <br> 2-methoxyoestradiol (EntreMed) <br> Arzoxifen (Eli Lilly) |
| Photodynamic agents | Talaporfin (Light Sciences) <br> Theralux (Theratechnologies) <br> Motexafin gadolinium (Pharmacyclics) | Pd-Bacteriopheophorbide (Yeda) <br> Lutetium texaphyrin (Pharmacyclics) <br> Hypericin |
| Tyrosine kinase inhibitors | Imatinib (Novartis) <br> Leflunomide (Sugen/Pharmacia) <br> ZDI839 (AstraZeneca) <br> Eriotinib (Oncogene Science) <br> Canertjnib (Pfizer) <br> Squalamine (Genaera) <br> SU5416 (Pharmacia) <br> SU6668 (Pharmacia) <br> ZD4190 (AstraZeneca) <br> ZD6474 (AstraZeneca) <br> Vatalanib (Novartis) <br> PKI166 (Novartis) <br> GW2016 (GlaxoSmithKline) <br> EKB-509 (Wyeth) <br> EKB-569 (Wyeth) | Kahalide F (PharmaMar) <br> CEP-701 (Cephalon) <br> CEP-751 (Cephalon) <br> MLN518 (Millenium) <br> PKC412 (Novartis) <br> Phenoxodiol O <br> Trastuzumab (Genentech) <br> C225 (ImClone) <br> rhu-Mab (Genentech) <br> MDX-H210 (Medarex) <br> 2C4 (Genentech) <br> MDX-447 (Medarex) <br> ABX-EGF (Abgenix) <br> IMC-1C11 (ImClone) |
| Various agents | SR-27897 (CCK-A inhibitor, Sanofi-Synthelabo) <br> Tocladesine (cyclic AMP agonist, Ribapharm) <br> Alvocidib (CDK inhibitor, Aventis) <br> CV-247 (COX-2 inhibitor, Ivy Medical) <br> P54 (COX-2 inhibitor, Phytopharm) <br> CapCell ™ (CYP450 stimulant, Bavarian Nordic) <br> GCS-IOO (gal3 antagonist, GlycoGenesys) <br> G17DT immunogen (gastrin inhibitor, Aphton) <br> Efaproxiral (oxygenator, Allos Therapeutics) <br> PI-88 (heparanase inhibitor, Progen) <br> Tesmilifen (histamine antagonist, YM BioSciences) <br> Histamine (histamine H2 receptor agonist, Maxim) <br> Tiazofurin (IMPDH inhibitor, Ribapharm) | BCX-1777 (PNP inhibitor, BioCryst) <br> Ranpirnase (ribonuclease stimulant, Alfacell) <br> Galarubicin (RNA synthesis inhibitor, Dong-A) <br> Tirapazamine (reducing agent, SRI International) <br> N-Acetylcysteine (reducing agent, Zambon) <br> R-Flurbiprofen (NF-kappaB inhibitor, Encore) <br> 3CPA (NF-kappaB inhibitor, Active Biotech) <br> Seocalcitol (vitamin D receptor agonist, Leo) <br> 131-I-TM-601 (DNA antagonist, TransMolecular) <br> Eflornithin (ODC inhibitor, ILEX Oncology) <br> Minodronic acid (osteoclast inhibitor, Yamanouchi) <br> Indisulam (p53 stimulant, Eisai) |

TABLE 1-continued

| | | |
|---|---|---|
| | Cilengitide (integrin antagonist, Merck KGaA) | Aplidin (PPT inhibitor, PharmaMar) |
| | SR-31747 (IL-1 antagonist, Sanofi-Synthelabo) | Rituximab (CD20 antibody, Genentech) |
| | CCI-779 (mTOR kinase inhibitor, Wyeth) | Gemtuzumab (CD33 antibody, Wyeth Ayerst) |
| | Exisulind (PDE-V inhibitor, Cell Pathways) | PG2 (haematopoiesis promoter, Pharmagenesis) |
| | CP-461 (PDE-V inhibitor, Cell Pathways) | Immunol ™ (triclosan mouthwash, Endo) |
| | AG-2037 (GART inhibitor, Pfizer) | Triacetyluridine (uridine prodrug, Wellstat) |
| | WX-UK1 (plasminogen activator-inhibitor, Wilex) | SN-4071 (sarcoma agent, Signature BioScience) |
| | PBI-1402 (PMN stimulant, ProMetic LifeSciences) | TransMID-107 ™ (immunotoxin, KS Biomedix) |
| | Bortezomib (proteasome inhibitor, Millennium) | PCK-3145 (apoptosis promoter, Procyon) |
| | SRL-172 (T-cell stimulant, SR Pharma) | Doranidazole (apoptosis promoter, Pola) |
| | TLK-286 (glutathione-S transferase inhibitor, Telik) | CHS-828 (cytotoxic agent, Leo) |
| | PT-100 (growth factor agonist, Point Therapeutics) | trans-Retinic acid (differentiator, NIH) |
| | Midostaurin (PKC inhibitor, Novartis) | MX6 (apoptosis promoter, MAXIA) |
| | Bryostatin-1 (PKC stimulants, GPC Biotech) | Apomine (apoptosis promoter ILEX Oncology) |
| | CDA-II (apoptosis promoter, Everlife) | Urocidin (apoptosis promoter Bioniche) |
| | SDX-101 (apoptosis promoter, Salmedix) | Ro-31-7453 (apoptosis promoter, La Roche) |
| | Ceflatonin (apoptosis promoter, ChemGenex) | Brostallicin (apoptosis promoter, Pharmacia) |
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 (Hoffmann-La Roche) |
| | Ormiplatin | |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharma) | BNP-1350 (BioNumerik) |
| | Rebeccamycin analogue (Exelixis) | CKD-602 (Chong Kun Dang) |
| | BBR-3576 (Novuspharma) | KW-2170 (Kyowa Hakko) |

TABLE 1-continued

| | | |
|---|---|---|
| Antitumour antibiotics | Dactinomycin (Actinomycin D)<br>Doxorubicin (Adriamycin)<br>Deoxyrubicin<br>Valrubicin<br>Daunorubicin (Daunomycin)<br>Epirubicin<br>Therarubicin<br>Idarubicin<br>Rubidazon<br>Plicamycinp<br>Porfiromycin<br>Cyanomorpholinodoxorubicin<br>Mitoxantron (Novantrone) | Amonafide<br>Azonafide<br>Anthrapyrazole<br>Oxantrazole<br>Losoxantrone<br>Bleomycin sulfate (Blenoxan)<br>Bleomycinic acid<br>Bleomycin A<br>Bleomycin B<br>Mitomycin C<br>MEN-10755 (Menarini)<br>GPX-100 (Gem Pharmaceuticals) |
| Antimitotic agents | Paclitaxel<br>Docetaxel<br>Colchicine<br>Vinblastine<br>Vincristine<br>Vinorelbine<br>Vindesine<br>Dolastatin 10 (NCI)<br>Rhizoxin (Fujisawa)<br>Mivobulin (Warner-Lambert)<br>Cemadotin (BASF)<br>RPR 109881A (Aventis)<br>TXD 258 (Aventis)<br>Epothilone B (Novartis)<br>T 900607 (Tularik)<br>T 138067 (Tularik)<br>Cryptophycin 52 (Eli Lilly)<br>Vinflunine (Fabre)<br>Auristatin PE (Teikoku hormone)<br>BMS 247550 (BMS)<br>BMS 184476 (BMS)<br>BMS 188797 (BMS)<br>Taxoprexin (Protarga) | SB 408075 (GlaxoSmithKline)<br>E7010 (Abbott)<br>PG-TXL (Cell Therapeutics)<br>IDN 5109 (Bayer)<br>A 105972 (Abbott)<br>A 204197 (Abbott)<br>LU 223651 (BASF)<br>D 24851 (ASTA Medica)<br>ER-86526 (Eisai)<br>Combretastatin A4 (BMS)<br>Isohomohalichondrin-B (PharmaMar)<br>ZD 6126 (AstraZeneca)<br>PEG-Paclitaxel (Enzon)<br>AZ10992 (Asahi)<br>!DN-5109 (Indena)<br>AVLB (Prescient NeuroPharma)<br>Azaepothilon B (BMS)<br>BNP- 7787 (BioNumerik)<br>CA-4-Prodrug (OXiGENE)<br>Dolastatin-10 (NrH)<br>CA-4 (OXiGENE) |
| Aromatase inhibitors | Aminoglutethimide<br>Letrozole<br>Anastrazole<br>Formestan | Exemestan<br>Atamestan (BioMedicines)<br>YM-511 (Yamanouchi) |
| Thymidylate synthase inhibitors | Pemetrexed (Eli Lilly)<br>ZD-9331 (BTG) | Nolatrexed (Eximias)<br>CoFactor ™ (BioKeys) |
| DNA antagonists | Trabectedin (PharmaMar)<br>Glufosfamide (Baxter International)<br>Albumin + 32P (Isotope Solutions)<br>Thymectacin (NewBiotics)<br>Edotreotid (Novartis) | Mafosfamide (Baxter International)<br>Apaziquone (Spectrum Pharmaceuticals)<br>O6-Benzylguanine (Paligent) |
| Farnesyl transferase inhibitors | Arglabin (NuOncology Labs)<br>Ionafarnib (Schering-Plough)<br>BAY-43-9006 (Bayer) | Tipifarnib (Johnson & Johnson)<br>Perillyl alcohol (DOR BioPharma) |
| Pump inhibitors | CBT-1 (CBA Pharma)<br>Tariquidar (Xenova)<br>MS-209 (Schering AG) | Zosuquidar trihydrochloride (Eli Lilly)<br>Biricodar dicitrate (Vertex) |
| Histone acetyl transferase inhibitors | Tacedinaline (Pfizer)<br>SAHA (Aton Pharma)<br>MS-275 (Schering AG) | Pivaloyloxymethyl butyrate (Titan)<br>Depsipeptide (Fujisawa) |
| Metalloproteinase inhibitors | Neovastat (Aeterna Laboratories)<br>Marimastat (British Biotech) | CMT -3 (CollaGenex)<br>BMS-275291 (Celltech) |
| Ribonucleoside reductase inhibitors | Gallium maltolate (Titan)<br>Triapin (Vion) | Tezacitabine (Aventis)<br>Didox (Molecules for Health) |
| TNF-alpha agonists/antagonists | Virulizin (Lorus Therapeutics)<br>CDC-394 (Celgene) | Revimid (Celgene) |
| Endothelin-A receptor antagonists | Atrasentan (Abbot)<br>ZD-4054 (AstraZeneca) | YM-598 (Yamanouchi) |
| Retinoic acid receptor agonists | Fenretinide (Johnson & Johnson)<br>LGD-1550 (Ligand) | Alitretinoin (Ligand) |
| Immunomodulators | Interferon<br>Oncophage (Antigenics)<br>GMK (Progenics) | Dexosome therapy (Anosys)<br>Pentrix (Australian Cancer Technology) |

TABLE 1-continued

| | | |
|---|---|---|
| | Adenocarcinoma vaccine (Biomira)<br>CTP-37 (AVI BioPharma)<br>JRX-2 (Immuno-Rx)<br>PEP-005 (Peplin Biotech)<br>Synchrovax vaccines (CTL Immuno)<br>Melanoma vaccine (CTL Immuno)<br>p21-RAS vaccine (GemVax) | JSF-154 (Tragen)<br>Cancer vaccine (Intercell)<br>Norelin (Biostar)<br>BLP-25 (Biomira)<br>MGV (Progenics)<br>!3-Alethin (Dovetail)<br>CLL-Thera (Vasogen) |
| Hormonal and antihormonal agents | Oestrogens<br>Conjugated oestrogens<br>Ethynyloestradiol<br>chlorotrianisene<br>Idenestrol<br>Hydroxyprogesteroncaproat<br><br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-methoxyoestradiol (EntreMed)<br>Arzoxifen (Eli Lilly) |
| Photodynamic agents | Talaporfin (Light Sciences)<br>Theralux (Theratechnologies)<br>Motexafin gadolinium (Pharmacyclics) | Pd-Bacteriopheophorbide (Yeda)<br>Lutetium-Texaphyrin (Pharmacyclics)<br>Hypericin |
| Tyrosine kinase inhibitors | Imatinib (Novartis)<br>Leflunomide(Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmithKline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-IOO (gal3 antagonist, GlycoGenesys)<br>G17DT immunogen (gastrin inhibitor, Aphton)<br>Efaproxiral (oxygenator, Allos Therapeutics)<br>PI-88 (heparanase inhibitor, Progen)<br>Tesmilifen (histamine antagonist, YM BioSciences)<br>Histamine (histamine H2 receptor agonist, Maxim)<br>Tiazofurin (IMPDH inhibitor, Ribapharm)<br>Cilengitide (integrin antagonist, Merck KGaA)<br>SR-31747 (IL-1 antagonist, Sanofi-Synthelabo)<br>CCI-779 (mTOR kinase inhibitor, Wyeth) | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore)<br>3CPA (NF-kappaB inhibitor, Active Biotech)<br>Seocalcitol (vitamin D receptor agonist, Leo)<br>131-I-TM-601 (DNA antagonist, TransMolecular)<br>Eflornithin (ODC inhibitor, ILEX Oncology)<br>Minodronic acid (osteoclast inhibitor, Yamanouchi)<br>Indisulam (p53 stimulant, Eisai)<br>Aplidin (PPT inhibitor, PharmaMar)<br>Rituximab (CD20 antibody, Genentech)<br>Gemtuzumab (CD33 antibody, Wyeth Ayerst) |

TABLE 1-continued

| | |
|---|---|
| Exisulind (PDE-V inhibitor, Cell Pathways) | PG2 (haematopoiesis promoter, Pharmagenesis) |
| CP-461 (PDE-V inhibitor, Cell Pathways) | Immunol ™ (triclosan mouthwash, Endo) |
| AG-2037 (GART inhibitor, Pfizer) | Triacetyluridine (uridine prodrug, Wellstat) |
| WX-UK1 (plasminogen activator-inhibitor, Wilex) | SN-4071 (sarcoma agent, Signature BioScience) |
| PBI-1402 (PMN stimulant, ProMetic LifeSciences) | TransMID-107 ™ (immunotoxin, KS Biomedix) |
| Bortezomib (proteasome inhibitor, Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) |
| PT-100 (growth factor agonist, Point Therapeutics) | trans-Retinic acid (differentiator, NIH) |
| Midostaurin (PKC inhibitor, Novartis) | MX6 (apoptosis promoter, MAXIA) |
| Bryostatin-1 (PKC stimulant, GPC Biotech) | Apomine (apoptosis promoter ILEX Oncology) |
| CDA-II (apoptosis promoter, Everlife) | Urocidin (apoptosis promoter Bioniche) |
| SDX-101 (apoptosis promoter, Salmedix) | Ro-31-7453 (apoptosis promoter, La Roche) |
| Ceflatonin (apoptosis promoter, ChemGenex) | Brostallicin (apoptosis promoter, Pharmacia) |

The compounds of the formula I are preferably combined with the with known anti-cancer agents:

These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and other angiogenesis inhibitors. The present compounds are particularly suitable for administration at the same time as radiotherapy. The synergistic effects of inhibition of VEGF in combination with radiotherapy have been described in the art (see WO 00/61186). "Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl] phenyl 2,2-dimethylpropanoate, 4,4'-dihydroxybenzophenone-2,4-dinitrophenylhydrazone and SH646. "Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumor necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, porfiromycin, cisplatin, irofulven, dexifosfamide, cisaminedichloro(2-methylpyridine)platinum, benzylguanine, glufosfamide, GPX100, (trans,trans,trans)bis-mu-(hexane-1,6-diamine)mu-[di-amineplatinum(II)]bis[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-Lvalyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino] ethyl]-5-[4-hydroxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumor suppressor genes, such as p53, which can be delivered via recombinant virus-mediated gene transfer (see U.S. Pat. No. 6,069,134, for example).

Particular preference is given to the use of the compound according to the invention for the treatment and prophylaxis of tumor diseases.

The tumor is preferably selected from the group of tumors of the squamous epithelium, of the bladder, of the stomach, of the kidneys, of head and neck, of the oesophagus, of the cervix, of the thyroid, of the intestine, of the liver, of the brain, of the prostate, of the urogenital tract, of the lymphatic system, of the stomach, of the larynx and/or of the lung.

The tumor is furthermore preferably selected from the group lung adenocarcinoma, small-cell lung carcinomas, pancreatic cancer, ovarian carcinoma, glioblastomas, colon carcinoma and breast carcinoma.

Preference is furthermore given to the use for the treatment of a tumor of the blood and immune system, preferably for the treatment of a tumor selected from the group of acute myeloid leukaemia, chronic myeloid leukaemia, acute lymphatic leukaemia and/or chronic lymphatic leukaemia.

In another aspect, the invention encompasses a for the treatment of a patient who has a neoplasm, such as a cancer, by administration of a compound of the formula (I) in combination with an antiproliferative agent. Suitable antiproliferative agents encompass those provided in Table 1.

Above and below, all temperatures are indicated in ° C. In the following examples, "conventional work-up" means: if necessary, water is added, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rt values are determined by HPLC using eluents mentioned.

Mass spectrometry (MS): EI (electron impact ionisation) $M^+$

FAB (fast atom bombardment) $(M+H)^+$

ESI (electrospray ionisation) $(M+H)^+$

APCI-MS (atmospheric pressure chemical ionisation—mass spectrometry) $(M+H)^+$ (A) HPLC Method (Non-Polar)
 Solvent A: water+0.1% of TFA
 Solvent B: acetonitrile+0.08% of TFA
 Flow: 1.5 ml/min
 Gradient: 0.0 min 20% of B
 5.0 min 100% of B
 5.5 min 100% of B
 6.0 min 20% of B
 6.5 min 20% of B
 Column: Chromolith Performance RP18e 100-3

(B) HPLC/MS Method (Polar)
 Solvent A: water+0.05% of formic acid
 Solvent B: acetonitrile+0.04% of formic acid
 Flow: 2.4 ml/min, wavelength: 220 nm
 Gradient: 0.0 min 4% of B
 2.8 min 100% of B
 3.3 min 100% of B
 3.4 min 4% of B
 Column: Chromolith® Speed ROD RP-18e 50-4.6 mm (C) HPLC Method
 Column: Chromolith SpeedROD, 50×4.6 $mm^2$ (OrderNo. 1.51450.0001) from Merck
 Gradient: 5.0 min, t=0 min, A:B=95:5, t=4.4 min: A:B=25:75, t=4.5 min to t=5.0 min: A:B=0:100
 Flow: 3.00 ml/min
 Eluent A: water+0.01% of HCOOH (formic acid)
 Eluent B: acetonitrile+0.01% of HCOOH
 Wavelength: 220 nm

EXAMPLE 1

Preparation of 3,5-dichlorobenzyl 4-{2-[(1H-benzotriazole-5-carbonyl)amino]-ethyl}piperazine-1-carboxylate (5)

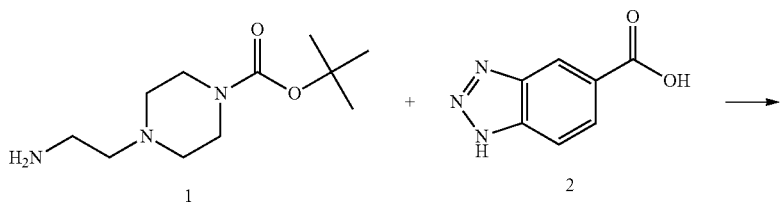

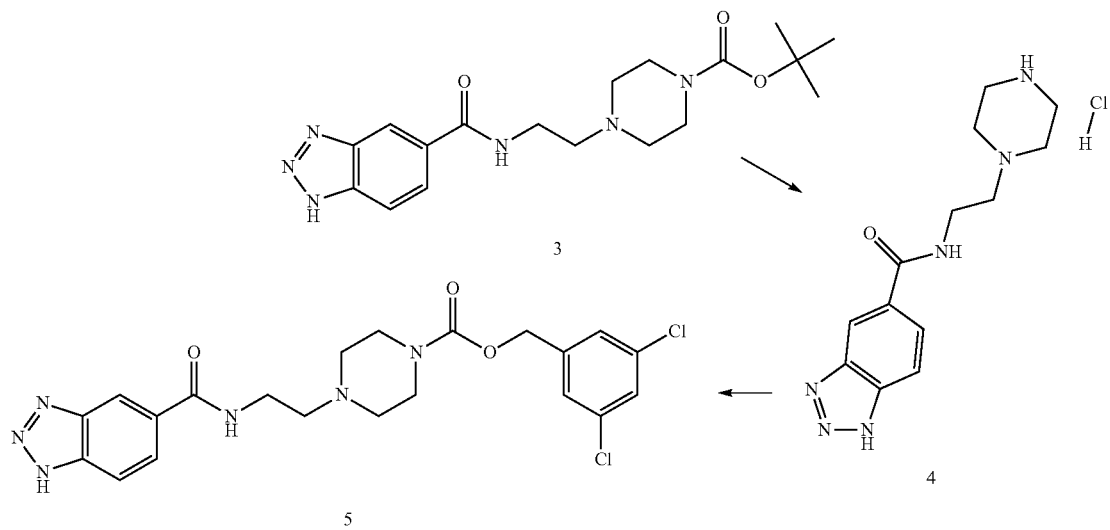

1.1 0.14 g (0.61 mmol) of 1, 0.12 g (0.74 mmol) of 2 and 0.2 ml of 4-methylmorpholine are dissolved in 6 ml of DMF. 0.14 g (0.73 mmol) of N-(3-dimethylaminopropyl)-N'-ethylcarbodiimide×HCl (DAPECI) and 0.1 g (0.74 mmol) of 1-hydroxybenzotriazole (HOBt) are then added. The mixture is stirred at RT for 18 h. The solvent is removed in a rotary evaporator, diluted with water (100 ml) and extracted 2× with EA. The organic phase is dried over magnesium sulfate, filtered off and evaporated to dryness, giving 0.21 g (92.3%) of 3 as brown crystals.

1.2 0.21 g (0.56 mmol) of 3 are dissolved in 20 ml of 5N HCl/isopropanol and stirred at RT for 2 h. In order to precipitate the product out completely, 20 ml of ether are added to the batch. The product is filtered off with suction and dried at 45° C. in a vacuum drying cabinet, giving 157 mg (80%) of brown crystals.

1.3 50 mg (0.28 mmol) of 3,5-dichlorobenzyl alcohol and 60 mg (0.37 mmol) of 1,1'-carbonyldiimidazole (CDI) are dissolved in 2 ml of DMF and stirred at RT for 3 h. 0.1 g (0.32 mmol) of 4 are then added and stirred at RT for 18 h. The mixture is washed with water. The organic phase is then dried over sodium sulfate, filtered off, and the solvent is evaporated in vacuo. The residue is purified by means of preparative HPLC, giving 62 mg (46%) of as pale-brown crystals.

EXAMPLE 2

Preparation of 3,5-dichlorobenzyl 4-{[(2-oxo-2,3-dihydrobenzoxazol-6-ylcarbamoyl)methyl]amino}piperidine-1-carboxylate (11)

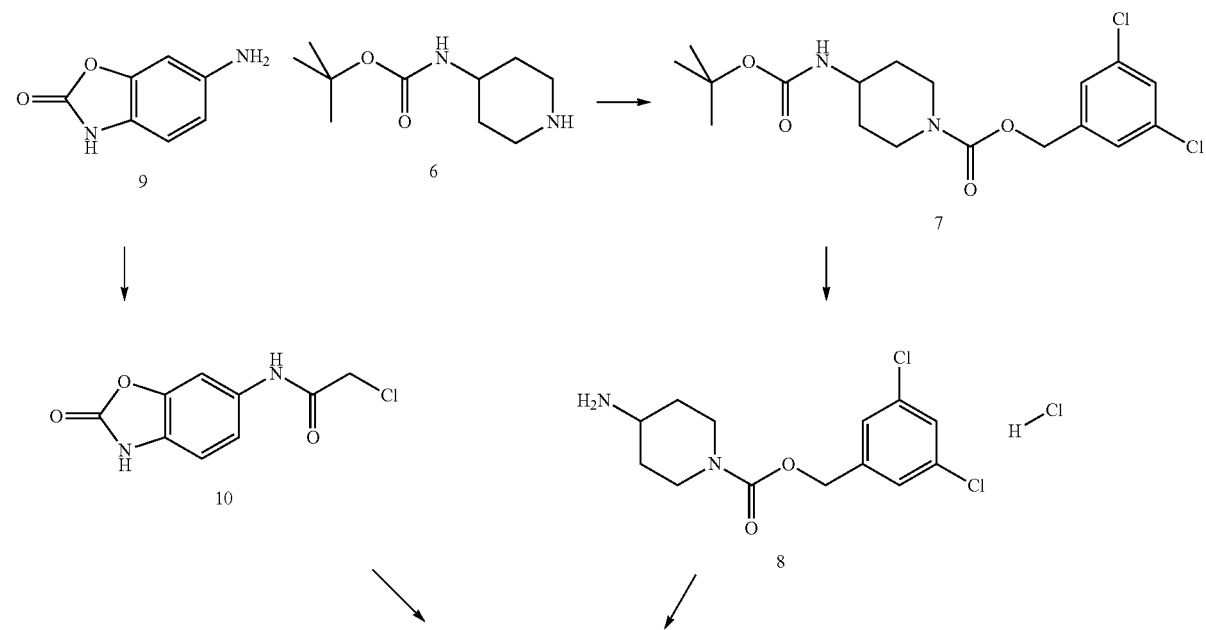

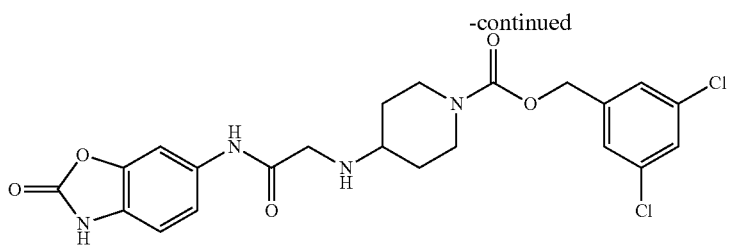

11

2.1 169.0 g (1.13 mol) of 9 and 470 ml of triethylamine (3.39 mol) are initially introduced in 2 l of methylene chloride (CH$_2$Cl$_2$). A solution of 128 g (1.13 mol) of chloroacetyl chloride in 1 l of CH$_2$Cl$_2$ is added with ice-cooling at such a rate that an internal temperature of 8° C. is not exceeded. The mixture is then boiled under reflux for 20 h. After the reaction mixture has been cooled, it is stirred with 3 l of water, during which a precipitate forms. The precipitate is filtered off with suction and washed with water and a little methanol, giving 183 g (71.7%) of 10 as amorphous solid substance.

2.2 0.5 g (2.8 mmol) of 3,5-dichlorobenzyl alcohol and 0.55 g (3.4 mmol) of 1,1' carbonyldiimidazole (CDI) are dissolved in 10 ml of CH$_2$Cl$_2$ and stirred at RT for 3 h. 0.56 g (2.8 mmol) of 6 are then added and stirred at RT for 18 h. The mixture is washed with water. The organic phase is then dried over sodium sulfate, filtered off, and the solvent is evaporated in vacuo. The residue is purified by means of preparative HPLC, giving 1.0 g (88%) of 7 as white crystals.

2.3 1.0 g (2.48 mmol) of 7 are dissolved in 100 ml of 5N HCl/isopropanol and stirred at RT for 2 h. In order to precipitate the product out completely, 200 ml of ether are added to the batch. The product is filtered off with suction and dried at 45° C. in a vacuum drying cabinet, giving 0.81 g (96%) of white crystals 8.

2.4 0.92 g (2.44 mmol) of 8 and 0.54 ml (3.9 mmol) of NEt$_3$ are initially introduced in 10 ml of DMF, then 0.56 g (2.44 mmol) of 10 are added. The mixture is stirred at RT for 48 h. 30 ml of water were added to the reaction mixture, the crystals which had precipitated out were filtered off with suction. Separation by column chromatography with CH$_2$Cl$_2$/MeOH gives 0.26 g (21%) of 11 as brown crystals;

RT [min] 3.68 (method A).

EXAMPLE 3

Preparation of 3,5-dichlorobenzyl 4-[3-hydroxy-3-(2-oxo-2,3-dihydrobenzoxazol-6-yl)propyl]piperazine-1-carboxylate (13)

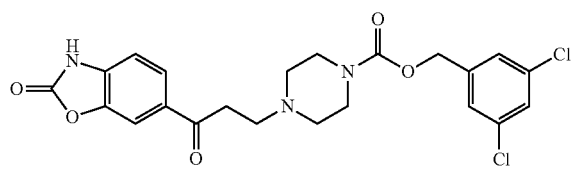

12

↓

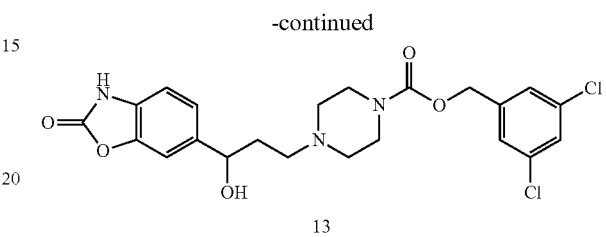

13

0.1 g of 12 (0.21 mmol) are dissolved in 5 ml of ethanol, then 30.0 mg (0.79 mmol) of sodium borohydride are added. The mixture is stirred at RT for 14 h. The solvent is then evaporated in vacuo, and the residue is purified by means of preparative HPLC, giving 66 mg (65%) of 13 as yellowish solid substance; RT [min] 3.57 (method A).

EXAMPLE 4

Preparation of 4-chlorobenzyl 4-[(Z)-3-chloro-3-(2-oxo-2,3-dihydrobenzoxazol-6-yl)allyl]piperazine-1-carboxylate (15)

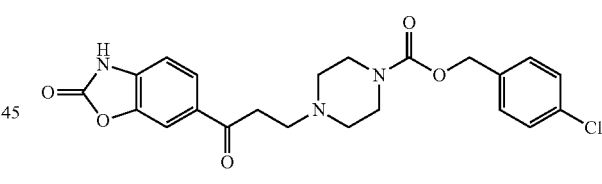

14

↓

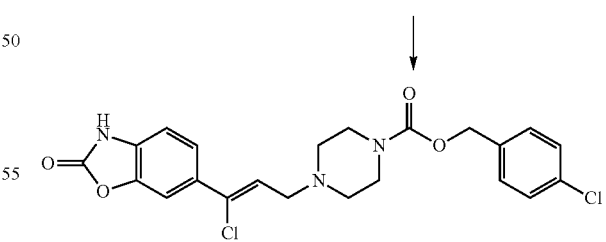

15

0.1 g of 14 (0.23 mmol) are mixed with 0.3 g (1.2 mmol) of 1,2-phenylenedioxytrichlorophosphorane and heated at 100° C. for 2 h. 5 ml of methanol are added to the dark-brown melt, and the mixture is treated in an ultrasound bath for 20 min, during which a pale-yellow solid substance precipitates out. This is filtered off with suction and, after drying at 45° C. in a drying cabinet, purified by means of preparative HPLC, giving 5.8 mg (6%) of 15 as yellowish solid substance; RT [min] 3.57 (method A).

EXAMPLE 5

Preparation of 4-chlorobenzyl 4-[3,3-difluoro-3-(2-oxo-2,3-dihydrobenzoxazol-6-yl)propyl]piperazine-1-carboxylate (17)

14 →

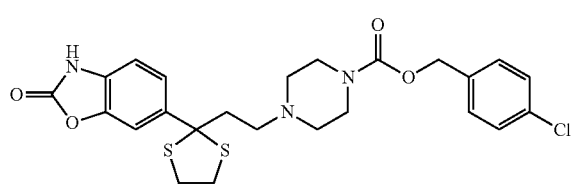

16

↓

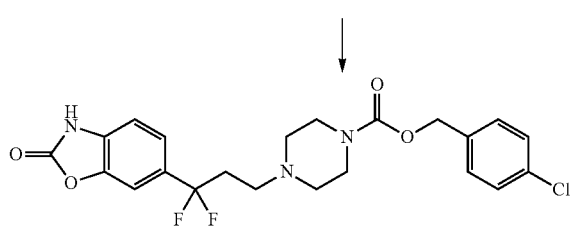

17

5.1 3.1 g (7.0 mmol) of 14 are dissolved in 2 ml of glacial acetic acid and 30 ml of DCM. With exclusion of air, 1.3 ml (15 mmol) of ethanedithiol are added, 0.98 ml (7 mmol) of boron trifluoride/acetic acid complex is subsequently added dropwise with exclusion of air. The mixture is stirred at RT for 72 h, and 50 ml of NaHCO$_3$ solution are then added. The crystals which have precipitated out are filtered off with suction. This is starting material. The organic phase is separated off, dried using MgSO$_4$. The organic phase is separated off, dried using MgSO$_4$ and evaporated in vacuo. Purification by column chromatography on silica gel with ethyl acetate gives 0.1 g (3%) of 16 as amorphous solid substance.

5.2 57 mg (0.2 mmol) of 1,3-dibromo-5,5-dimethylhydantoin are initially introduced in 3 ml of dichloromethane. 0.23 ml (4 mmol) of pyridine/hydrogen fluoride is added at −78° C. with exclusion of air. 100 mg (0.19 mmol) of 16, suspended in 5 ml of dichloromethane, are then added. Stirring is continued for 20 min. The cooling is then removed, and 15 ml of NaHCO$_3$ solution are added to the reaction mixture. The organic phase is separated off, dried using MgSO$_4$ and evaporated in vacuo. Purification by means of preparative HPLC gives 15 mg (17%) of 17 as solid substance; RT [min] 2.96 (method C).

EXAMPLE 6

Preparation of 3,5-dichlorobenzyl 4-{2-[3-(2-oxo-2,3-dihydrobenzoxazol-6-yl)-4,5-dihydropyrazol-1-yl]ethyl}piperazine-1-carboxylate (21)

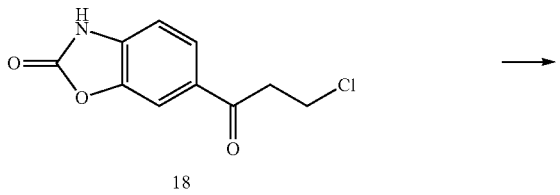

18

→

19

↓

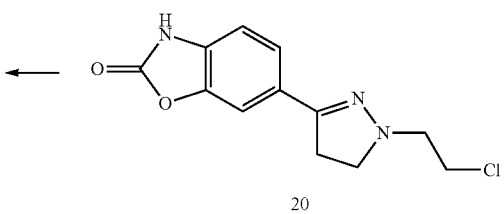

20

←

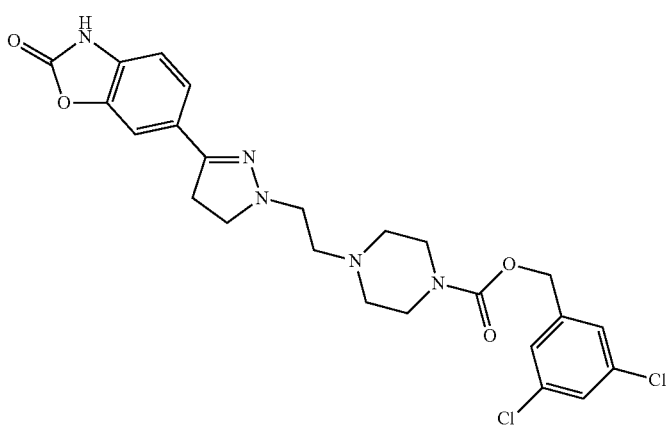

21

6.1 10.0 g (44 mmol) of 18 are dissolved in 100 ml of ethanol. 4.0 g (52 mmol) of hydroxyethylhydrazine and subsequently 7.0 ml (53 mmol) of triethylamine are then added. The mixture is stirred at RT for 2 h. The resultant yellow precipitate is filtered off with suction and dried at 45° C. in a vacuum drying cabinet, giving 4.1 g (37.4%) of 19 as yellow crystals.

6.2 0.5 g (2.0 mmol) of 19 are dissolved in 10 ml of DMF. 0.5 ml (6.9 mmol) of thiony chloride is then added, and the mixture is stirred at RT for 30 min. The reaction mixture is evaporated in vacuo. The residue is triturated with 10 ml of acetonitrile, the crystals are filtered off with suction and dried in air, giving 0.32 g (60%) of 20 as greenish crystals.

6.3 0.12 g (0.4 mmol) of 20, 0.13 g (0.4 mmol) of 3,5-dichlorobenzyl piperazine-1-carboxylate and 0.1 g (1.2 mmol) of NaHCO$_3$ are stirred at 100° C. for 16 h in 3 ml of acetonitrile. After cooling, 20 ml of water are added to the reaction mixture, which is then extracted twice with CH$_2$Cl$_2$. The organic phase is dried using NaSO$_4$ and evaporated in vacuo. Purification by column chromatography on silica gel with ethyl acetate/methanol gives 21 mg (10%) of 21 as yellow-brown crystals; RT [min] 2.80 (method A).

EXAMPLE 7

Preparation of 4-chlorobenzyl 4-(2-1H-benzotriazol-5-ylacetyl)piperazine-1-carboxylate (24)

7.1 5.0 g (26 mmol) of ethyl 3,4-diaminophenylacetate are dissolved in 40 ml of 50% acetic acid and cooled in an ice bath. 2.7 g (39 mmol) of sodium nitrite in 20 ml of water are added dropwise at such a rate that the temperature remains below 10° C. The mixture is stirred at 10°-20° C. for 3 h. The batch is then diluted with 200 ml of ethyl acetate and washed with water. The organic phase is dried using NaSO$_4$. and evaporated in vacuo, giving 5.7 g (108%) of 22 as brown oil (also contains a little solvent).

7.2 5.7 g (28 mmol) of 22 are dissolved in 25 ml of water and 10 ml of EtOH, and 75 ml of 5% aqueous NaOH solution are added. The mixture is heated under reflux for 3 h. After cooling, the mixture is evaporated in vacuo. The residue is dissolved in 100 ml of water and adjusted to pH 4 using 5-6 N HCl in propanol. The crystals which have precipitated out are filtered off with suction, giving 3.3 g (56%) of 23 as brown crystals.

7.3 220 mg (1.24 mmol) of 23, 362 mg (1.24 mmol) of 4-chlorobenzyl piperazine-1-carboxylate hydrochloride, 168 mg (1.24 mmol) of 1-hydroxybenzotriazole (HOBt), 143 mg (1.24 mmol) of N-methylmorpholine and 238 mg (1.24 mmol) of 3-dimethylaminopropylcarbodiimide hydrochloride (DAPECI) are stirred at RT for 48 h in 10 ml of DMF.

The reaction mixture is then evaporated in vacuo. Purification by means of preparative HPLC gives 16 mg (3%) of 24 as colourless solid substance; RT [min] 3.73 (method A);

$^1$H-NMR (DMSO-d$_6$) δ [ppm] 7.86 (d, J=8.5, 1H), 7.75 (d, J=1.4, 1H), 7.46-7.36 (m, 4H), 7.34 (dd, J=8.5, 1.4, 1H), 5.10 (s, 2H), 3.95 (s, 2H), 3.65-3.30 (m, 7H).

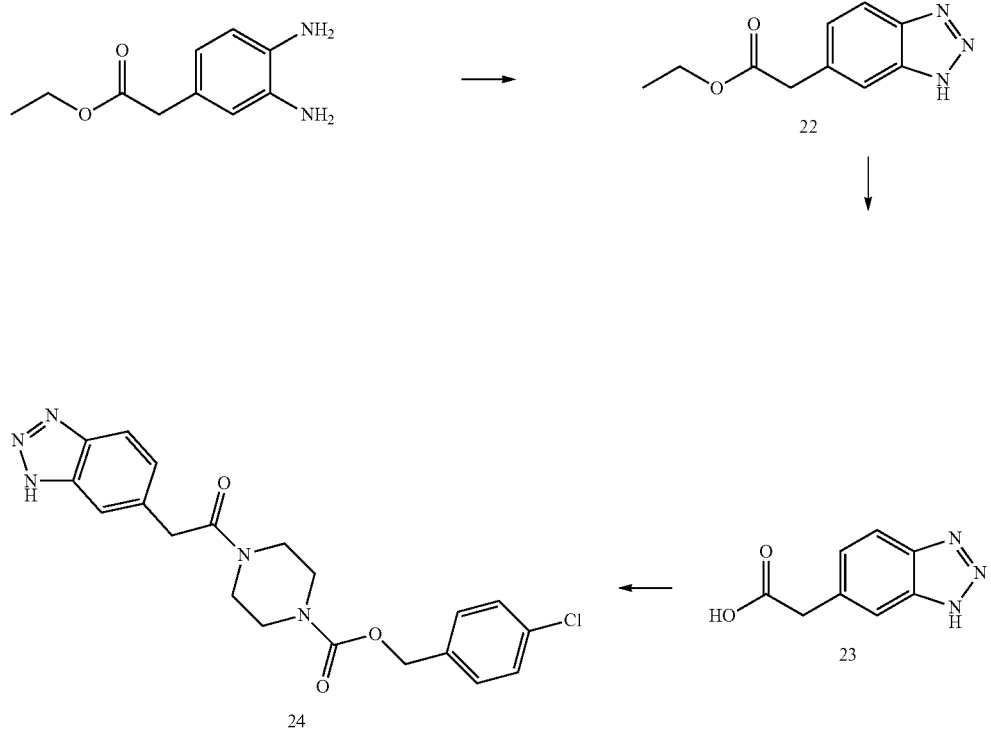

EXAMPLE 8

Preparation of 6-(2-{4-[3-(4-chlorophenoxy)propionyl]piperazin-1-yl}acetyl)-3H-benzoxazol-2-one (27)

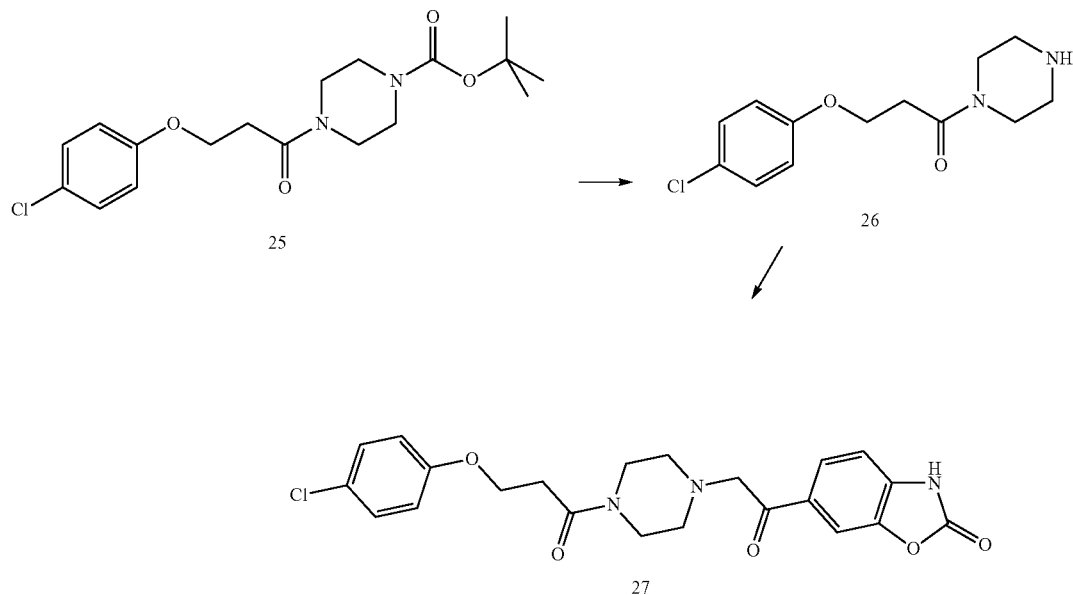

8.1 500 mg (2.5 mmol) of 3-(4-chlorophenoxy)propionic acid, 464 mg (2.5 mmol) of Boc-piperazine and 253 mg (2.5 mmol) of 4-methylmorpholine are initially introduced in 3 ml of DMF. 478 mg (2.5 mmol) of DAPECI and 337 mg (2.5 mmol) of HOBt are then added, and the mixture is stirred at RT for 16 h. The reaction mixture is poured onto water, and the resultant precipitate is filtered off with suction and dried, giving 894 mg (97%) of 25.

8.2 894 mg (2.4 mmol) of 25 are introduced into 10 ml of 5-6N HCl in propanol and stirred at RT for 0.5 h. The resultant precipitate is filtered off with suction and dried giving 661 mg (89%) of 26.

8.3 104 mg (0.49 mmol) of 6-(2-chloroacetyl)-3H-benzoxazolone (synthesis described under file reference 102007047737.8 at the German Patent Office) are initially introduced in 3 ml of acetonitrile. 150 mg (1.5 mmol) of triethylamine and 150 mg (0.49 mmol) of 26 are then added, and the mixture is stirred at RT for 16 h and at 80° C. for a further 16 h. The resultant precipitate is filtered off, and the filtrate is evaporated in vacuo. Purification by column chromatography on silica gel with EA gives 6 mg (3%) of 27; RT [min] 3.04 (method A);

$^1$H-NMR (DMSO-$d_6$) δ [ppm] 11.66 (s, 1H), 7.90-7.84 (m, 2H), 7.31 (d, J=9.0, 2H), 7.19 (d, J=7.6, 1H), 6.95 (d, J=9.0, 2H), 4.18 (t, J=6.2, 2H), 3.86 (s, 2H), 3.62-3.30 (m, 8H), 2.80 (t, J=6.2, 2H).

EXAMPLE 9

Preparation of 4-chlorobenzyl 4-[2-(1H-benzotriazol-5-ylcarbamoyl)ethyl-carbamoyl]piperidine-1-carboxylate (32)

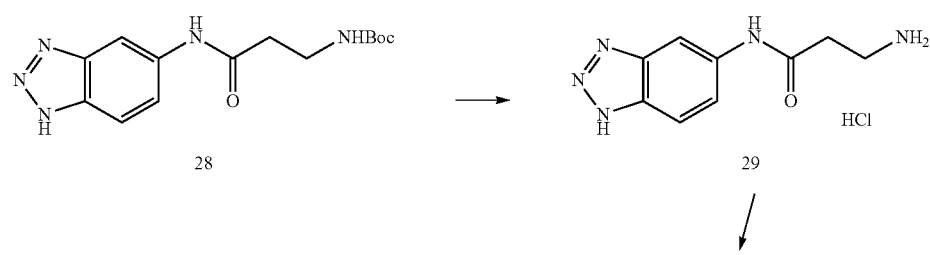

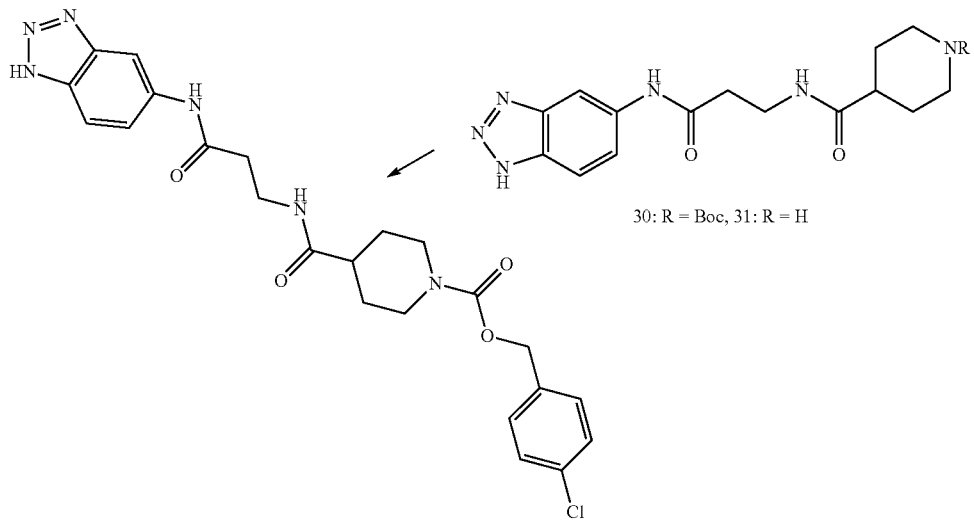

30: R = Boc, 31: R = H

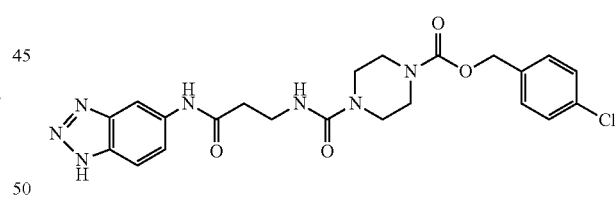

32

9.1 2.7 g (20 mmol) of 5-aminobenzotriazole, 3.8 g (20 mmol) of 3-tert-butoxycarbonylaminopropionic acid, 3.5 g of HOBt (26 mmol) and 4.2 g (22 mmol) of DAPECI are dissolved in 30 ml of DMF and stirred at RT for 16 h. The reaction mixture is then evaporated in vacuo. The residue is taken up in 200 ml of ethyl acetate and washed by shaking twice with water. The organic phase is dried using MgSO$_4$ and evaporated in vacuo. Purification by column chromatography on silica gel with ethyl acetate gives 5.7 g (93%) of 28.

9.2 5.7 g (19 mmol) of 28 are dissolved in 60 ml of 6N HCl in isopropanol and stirred at RT for 1 h. The reaction mixture is then evaporated in vacuo. The residue is triturated with methylene chloride and filtered off with suction, giving 4.1 g (91%) of 29 as pale-brown amorphous solid substance.

9.3 0.97 g (4.0 mmol) of 29, 0.92 g (4.0 mmol) of 1-butoxycarbonyl-piperidine-4-carboxylic acid, 0.54 g of HOBt (4.0 mmol) and 0.77 g (4.0 mmol) of DAPECI and 0.55 ml of triethylamine (4.0 mmol) are dissolved in 10 ml of DMF and stirred at RT for 16 h. The reaction mixture is then evaporated in vacuo. The residue is taken up in 100 ml of ethyl acetate and washed by shaking twice with water. The organic phase is dried using MgSO$_4$ and evaporated in vacuo. Purification by column chromatography on silica gel with ethyl acetate gives 1.4 g (84%) of 30.

9.4 1.4 g (3.4 mmol) of 30 are dissolved in 20 ml of 6 N HCl in isopropanol and stirred at RT for 1 h. The reaction mixture is then evaporated in vacuo, giving 1.1 g (93%) of 31 as brown amorphous solid substance.

9.5 81 mg (0.5 mmol) of CDI and 78 mg (0.5 mmol) of 4-chlorobenzyl alcohol are dissolved in 3 ml of DMF and stirred at RT for 2 h. 176 mg (0.5 mmol) of 31 are then added, and the mixture is stirred at RT for 16 h. The reaction mixture is then evaporated in vacuo. The residue is taken up in 20 ml of ethyl acetate and washed by shaking twice with water. The organic phase is dried using MgSO$_4$ and evaporated in vacuo.

The residue is crystallised using ethanol, giving 77 mg (32%) of 32 as pale-brown crystals; RT [min] 3.36 (method C).

EXAMPLE 10

Preparation of 4-chlorobenzyl 4-[2-(1H-benzotriazol-5-ylcarbamoyl)ethyl-carbamoyl]piperazine-1-carboxylate (33)

33

121 mg (0.5 mmol) of 29 are initially introduced in 3 ml of DMF with 0.035 ml of triethylamine, and 81 mg (0.5 mmol) of CDI are added. The mixture is stirred at RT for 1 h, and 146 mg (0.5 mmol) of 4-chlorobenzyl piperazine-1-carboxylate hydrochloride and a further 0.035 ml of triethylamine are then added. The mixture is then stirred at RT for 2 h. The reaction mixture is then evaporated in vacuo. The residue is taken up in 20 ml of ethyl acetate and washed by shaking twice with water. The organic phase is dried using MgSO$_4$ and evaporated in vacuo. The residue is recrystallised from ethanol, giving 81 mg (33%) of 33 as pale-brown crystals; RT [min] 3.25 (method C).

EXAMPLE 11

Preparation of 4-chlorobenzyl 4-[2-(1H-benzotriazol-5-ylcarbamoyl)acetylamino]piperidine-1-carboxylate (39)

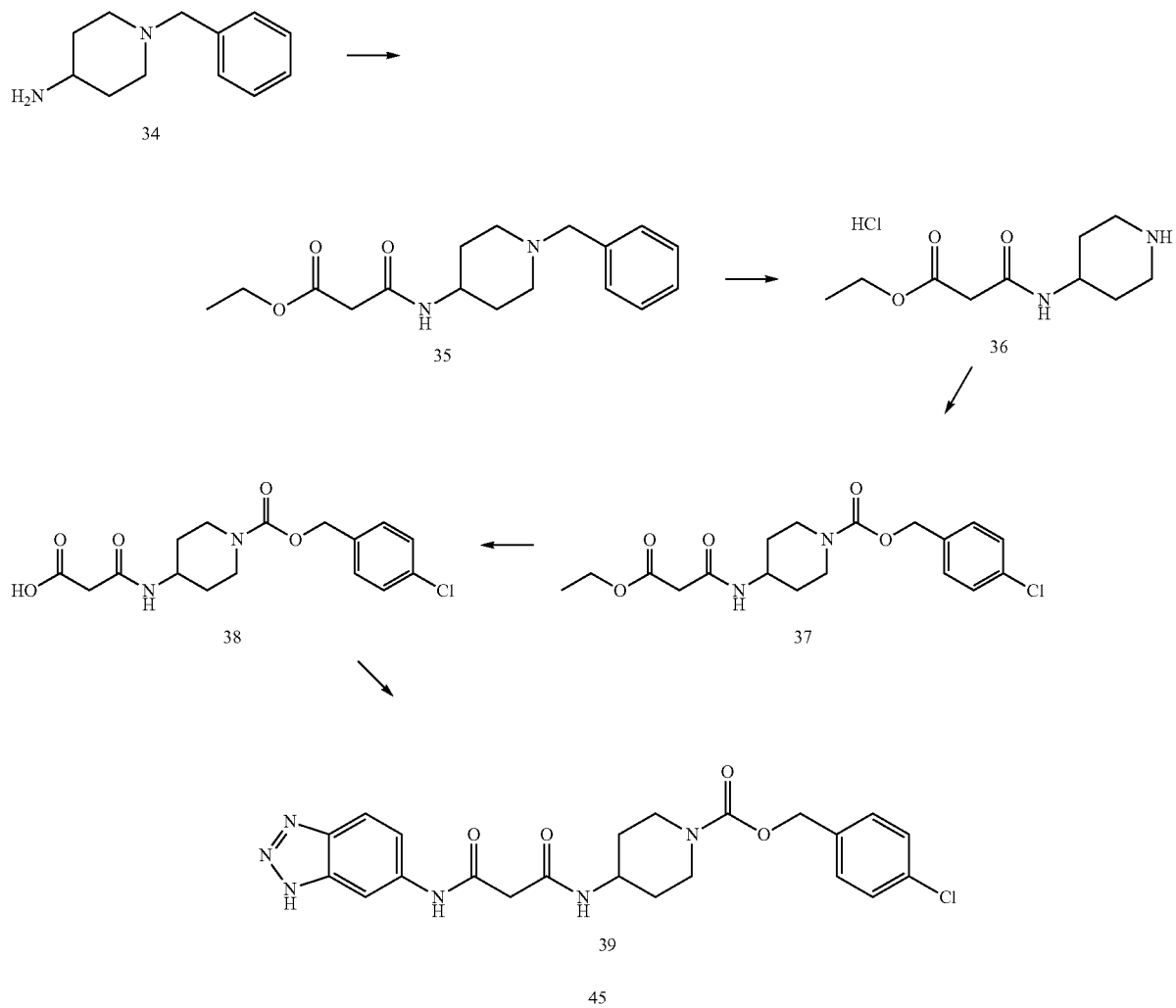

11.1 5.23 g (27.5 mmol) of 34 and 3.8 ml (27.5 mmol) of triethylamine are initially introduced in 50 ml of methylene chloride. 4.14 g (27.5 mmol) of ethyl malonate chloride are added dropwise with ice-cooling, and the mixture is then stirred at RT for a further 1 h. The reaction mixture is extracted with water, the organic phase is then separated off, dried using $NaSO_4$ and evaporated in vacuo. Purification by column chromatography on silica gel with ethyl acetate gives 2.85 (34%) of 35 as colourless crystals.

11.2 2.0 g (6.6 mmol) of 35 are dissolved in 20 ml of THF and 20 ml of glacial acetic acid, 2 g of 5% Pd/C are added, and the mixture is hydrogenated. The catalyst is filtered off. 6N HCl is added, and the solvent is then evaporated in vacuo, giving 1.6 g (97%) of 36 as solid substance.

11.3 1.5 g (10.5 mmol) of 4-chlorobenzyl alcohol, 1.7 g (10.5 mmol) of CDI are stirred at RT for 2 h in 10 ml of DMF. 1.04 ml (7.5 mmol) of triethylamine and 1.6 g (7.5 mmol) of 36 are then added, and the mixture is stirred at RT for 16 h. The reaction mixture is then added to water. The resultant precipitate is filtered off with suction and purified by column chromatography on silica gel with petroleum ether/ethyl acetate (1:1), giving 1.46 g (51%) of 37 as pale-yellow crystals.

11.4 1.46 g (3.8 mmol) of 37 are dissolved in 10 ml of ethanol, 3.0 ml of aqueous 2N NaOH are added, and the mixture is stirred at RT for 16 h. The solution is acidified using 1N HCl and evaporated in a rotary evaporator. The residue is taken up using ethyl acetate and washed with water. The organic phase is dried using NaSO4 and evaporated in a rotary evaporator, giving 0.47 g (35%) of 38 as amorphous solid substance.

11.5 0.47 g (1.32 mmol) of 38, 0.178 g (1.32 mmol) of 5-aminobenzotriazole, 0.28 g (1.46 mmol) of DAPECI and 0.20 g (1.46 mmol) of HOBt are dissolved in 5 ml of DMF and stirred at RT for 16 h. The reaction mixture is then evaporated in vacuo. The residue is taken up in 20 ml of ethyl acetate and washed by shaking twice with water. The organic phase is dried using $MgSO_4$. and evaporated in vacuo. A white precipitate precipitates out in the process and is filtered off with suction and dried, giving 0.14 g (22%) of 39 as colourless solid substance; RT [min] 3.33 (method C).

The following compounds are obtained analogously to the above examples
the following compounds

| No. | Structure and/or name | RT [min] (method) |
|---|---|---|
| "A1" | 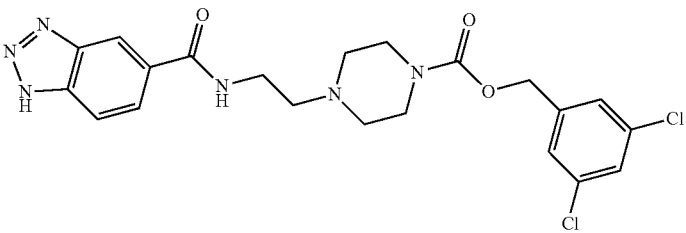 [SMILES: O=C(NCCN1CCN(C(=O)OCc2cc(Cl)cc(Cl)c2)CC1)c1ccc2[nH]nnc2c1]<br>3,5-Dichlorobenzyl 4-{2-[(1H-benzotriazole-5-carbonyl)amino]ethyl}piperazine-1-carboxylate | 3.23 (A) |
| "A2" | 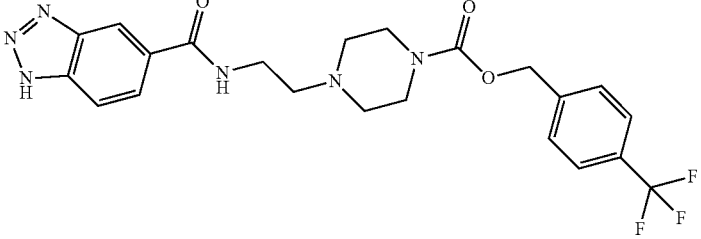<br>4-Trifluoromethylbenzyl 4-{2-[(1H-benzotriazole-5-carbonyl)amino]ethyl}piperazine-1-carboxylate | 3.28 (A) |
| "A3" | 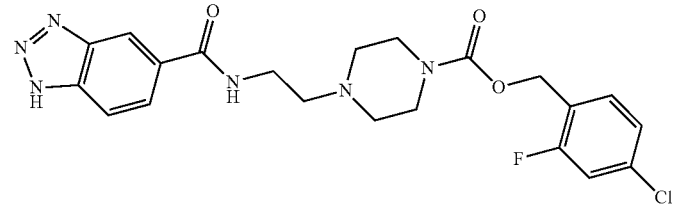 [SMILES: O=C(NCCN1CCN(C(=O)OCc2ccc(Cl)cc2F)CC1)c1ccc2[nH]nnc2c1]<br>4-Chloro-2-fluorobenzyl 4-{2-[(1H-benzotriazole-5-carbonyl)amino]ethyl}piperazine-1-carboxylate | 3.12 (A) |

$^{1}$H-NMR (DMSO-d$_{6}$) δ [ppm] 8.61 (t, J = 5.6, 1H), 8.44 (s, 1H), 7.94 (s, 2H) 7.58-7.41 (m, 3H), 7.34-7.27 (m, 1H), 5.10 (s, 2H), 3.47-3.39 (m, 6H), 2.53 (t, J = 7.0, 2H), 2.47-2.38 (m, 4H)

| | | |
|---|---|---|
| "A4" | 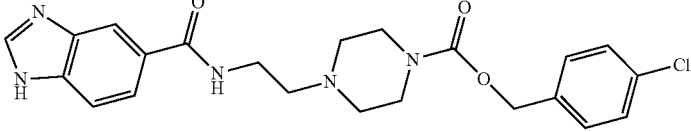<br>4-Chlorobenzyl 4-{2-[(1H-benzimidazole-5-carbonyl)amino]ethyl}piperazine-1-carboxylate hydrochloride | 2.72 (A) |

$^{1}$H-NMR (DMSO-d$_{6}$) δ [ppm] 9.75 (s, 1H), 8.37 (d, J = 1.0, 1H), 8.12 (dd, J = 8.7, 1.0, 1H), 7.99 (d, J = 8.7, 1H), 7.44 (s, 4H), 5.14 (s, 2H), 4.25-4.10 (n, 2H), 3.73 (t, J = 7.0 Hz, 2H), 3.71-3.56 (m, 2H), 3.40-3.1 (m, 6H)

| | | |
|---|---|---|
| "A5" | 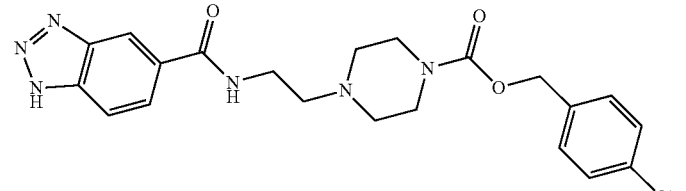<br>4-Chlorobenzyl 4-{2-[(1H-benzotriazole-5-carbonyl)-amino]ethyl}piperazine-1-carboxylate | 3.15 (A) |

| No. | Structure and/or name | RT [min] (method) |
|---|---|---|
| "A6" | 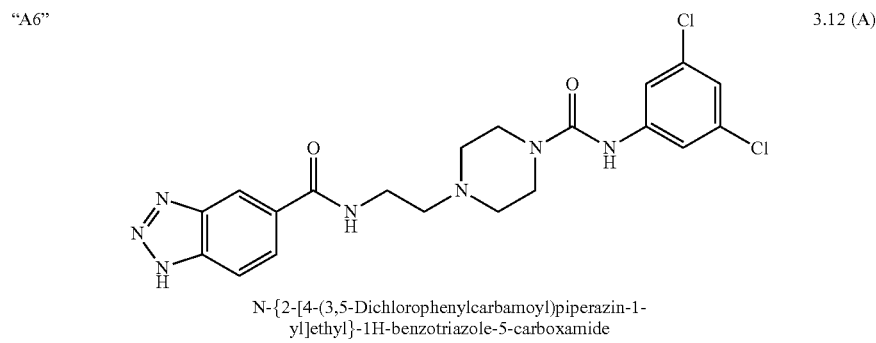<br>N-{2-[4-(3,5-Dichlorophenylcarbamoyl)piperazin-1-yl]ethyl}-1H-benzotriazole-5-carboxamide | 3.12 (A) |
| "A7" | 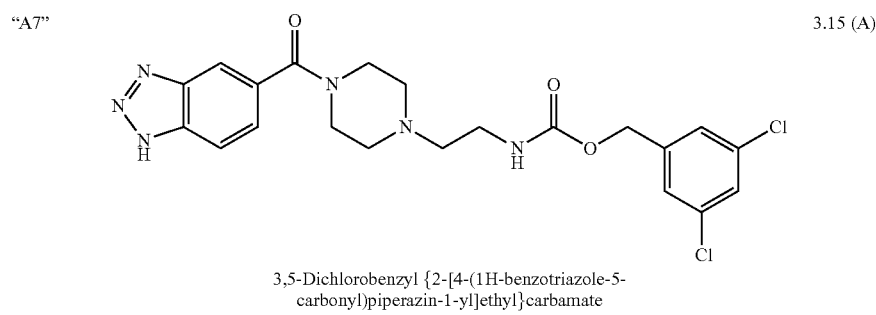<br>3,5-Dichlorobenzyl {2-[4-(1H-benzotriazole-5-carbonyl)piperazin-1-yl]ethyl}carbamate | 3.15 (A) |

$^1$H-NMR (DMSO-$d_6$) δ [ppm]8.12 (s, 1H), 7.97 (d, J = 8.6 Hz, 1H), 7.56 (d, J = 8.6, 1H), 7.46-7.39 (m, 3H), 5.11 (s, 2H), 3.72-3.20 (m, 12H [identified in there: 3.52 (t, J = 5.8, 2H), 3.32 (t, J = 5.8, 2H)]

| | | |
|---|---|---|
| "A8" | 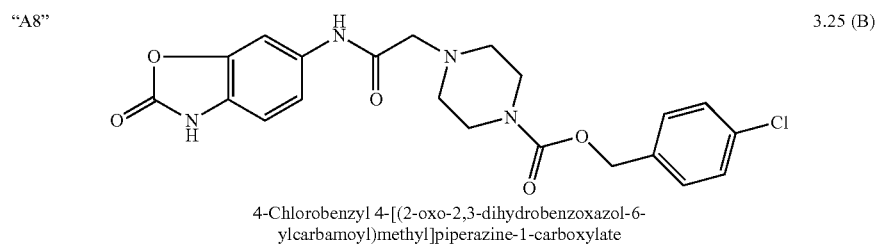<br>4-Chlorobenzyl 4-[(2-oxo-2,3-dihydrobenzoxazol-6-ylcarbamoyl)methyl]piperazine-1-carboxylate | 3.25 (B) |

$^1$H-NMR (DMSO-$d_6$) δ [ppm] 7.67 (d, J = 1.8, 1H), 7.40 (s, 4H), 7.20 (dd, J = 8.4, 1.9, 2H), 7.06 (d, J = 8.4, 1H), 5.10 (s, 2H), 4.18 (s, 2H), 3.68-3.04 (m, 7H)

| | | |
|---|---|---|
| "A9" | 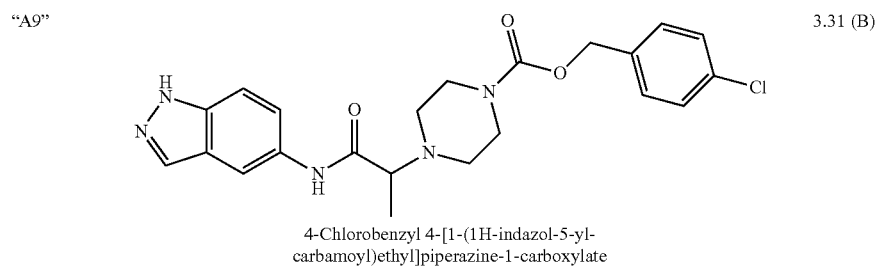<br>4-Chlorobenzyl 4-[1-(1H-indazol-5-yl-carbamoyl)ethyl]piperazine-1-carboxylate | 3.31 (B) |

-continued

| No. | Structure and/or name | RT [min] (method) |
|---|---|---|
| "A10" | 4-Chlorobenzyl 4-[(2-oxo-2,3-dihydrobenzoxazol-6-ylcarbamoyl)phenylmethyl]piperazine-1-carboxylate | 3.89 (B) |
| "A11" | 4-Chlorobenzyl 4-[1-(1H-indol-5-ylcarbamoyl)ethyl]-piperazine-1-carboxylate | 3.79 (B) |
| "A12" | 4-Chlorobenzyl 4-[1-(1H-indazol-5-ylcarbamoyl)-1-methylethyl]piperazine-1-carboxylate | 3.41 (A) |
| "A13" | 4-Chlorobenzyl 4-[2-(2-oxo-2,3-dihydrobenzoxazol-6-ylcarbamoyl)ethyl]piperazine-1-carboxylate | 3.28 (B) |
| "A14" | 4-Chlorobenzyl 4-[3-(1H-benzotriazol-5-yl-carbamoyl)propyl]piperazine-1-carboxylate | 2.35 (C) |

-continued

| No. | Structure and/or name | RT [min] (method) |
|---|---|---|

"A15"

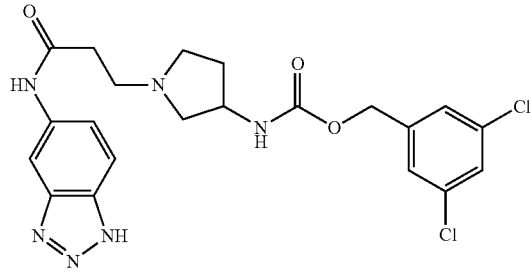 [SMILES: O=C(CCN1CCC(NC(=O)OCc2cc(Cl)cc(Cl)c2)C1)Nc1ccc2[nH]nnc2c1]

3,5-Dichlorobenzyl {1-[2-(1H-benzotriazol-5-yl-carbamoyl)ethyl]pyrrolidin-3-yl}carbamate 3.25 (A)

$^1$H-NMR (DMSO-$d_6$) δ [ppm] 10.31 (s, 1H), 8.36 (s, 1H), 7.86 (d, J = 8.9, 1H), 7.64 (s, 1H), 7.56 (s, 1H), 7.42 (s, 2H), 7.35 (d, J = 8.9, 1H), 5.02 (s, 2H), 4.05-3.89 (m, 2H), 2.86-2.68 (m, 4H), 2.68-2.56 (m, 2H), 2.47-2.31 (m, 2H), 2.19-2.02 (m, 1H), 1.66-1.56 (m, 1H)

"A16"

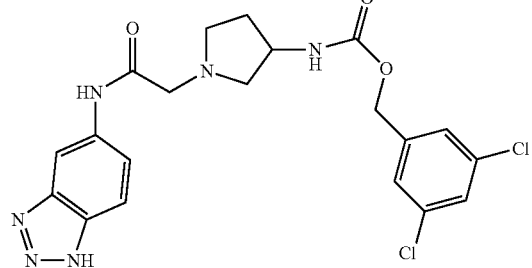

3,5-Dichlorobenzyl {1-[(1H-benzotriazol-5-yl-carbamoyl)methyl]pyrrolidin-3-yl}crbamate 3.25 (A)

$^1$H-NMR (DMSO-$d_6$) δ [ppm] 15.52 (s, 1H), 9.97 (s, 1H), 8.35 (s, 1H), 7.90 (s, 1H), 7.70 (d, J = 7.4, 1H), 7.61-7.35 (m, 4H), 5.04 (s, 2H), 4.05 (s, 1H), 3.45-3.35 (m, 2H, covered by water), 2.89-2.77 (m, 2H), 2.63-2.53 (m, 2H) 2.22-2.12 (m, 1H), 1.72-1.63 (m, 1H)

"A17"

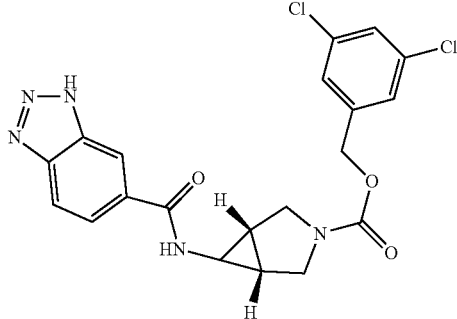 [SMILES: O=C(NC1[C@H]2CN(C(=O)OCc3cc(Cl)cc(Cl)c3)C[C@@H]12)c1ccc2nn[nH]c2c1]

3,5-Dichlorobenzyl (1R,5S)-6-[(3H-benzotriazole-5-carbonyl)amino]-3-azabicyclo[3.1.0]hexane-3-carboxylate 3.92 (A)

$^1$H-NMR (DMSO-$d_6$) δ [ppm] 15.91 (s, 1H), 8.70 (d, J = 3.8, 1H), 8.42 (s, 1 H), 7.91 (s, 2H), 7.56 (s, 1H), 7.43 (d, J = 1.6, 2H), 5.07 (d, J = 5.2, 2H), 3.67 (d, J = 10.7, 1H), 3.61 (d, J = 10.7, 1H), 3.54 (dd, J = 10.7, 2.6, 1H), 3.47 (dd, J = 10.7, 2.6, 1H), 2.63 (s, 1H), 1.97-1.82 (m, 2H)

| No. | Structure and/or name | RT [min] (method) |
|---|---|---|
| "A18" | 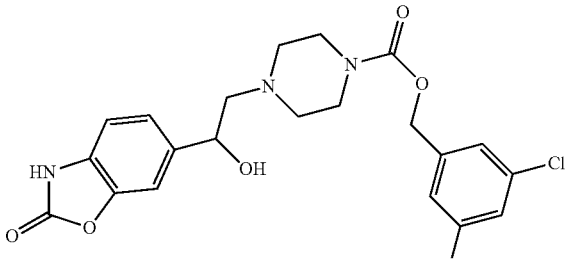<br>3,5-Dichlorobenzyl 4-[2-hydroxy-2-(2-oxo-2,3-dihydrobenzoxazol-6-yl)ethyl]piperazine-1-carboxylate | 3.49 (A) |

$^1$H-NMR (DMSO-$d_6$) δ [ppm] 11.50 (s, 1H), 7.56 (t, J = 1.9, 1H), 7.41 (d, J = 1.9, 2H), 7.24 (d, J = 1.1, 1H), 7.12 (dd, J = 8.0, 1.1, 1H), 7.01 (d, J = 8.0, 1H), 5.09 (d, J = 4.0, 1H), 5.07 (s, 2H), 4.74-4.70 (m, 1H), 3.50-3.30 (m, 8H), 2.49-2.38 (m, 2H)

Pharmacological Data
Autotaxin Inhibition (Enzyme Test)

TABLE 1

| Compound No. | IC50 |
|---|---|
| "11" | B |
| "13" | B |
| "15" | |
| "17" | B |
| "21" | C |
| "24" | C |
| "27" | C |
| "32" | |
| "33" | C |
| "39" | B |
| "A1" | B |
| "A2" | C |
| "A3" | C |
| "A4" | |
| "A5" | |
| "A6" | |
| "A7" | |
| "A8" | C |
| "A9" | |
| "A10" | C |
| "A11" | |
| "A12" | |
| "A13" | C |
| "A14" | C |
| "A15" | |
| "A16" | C |
| "A17" | C |
| "A18" | C |

IC50: <100 nM = A
100 nM-1 μM = B
>1 μM = C

EXAMPLE A

Autotaxin Test (Enzyme Test)

Test Description

The autotaxin activity is measured indirectly using Amplex Red reagent. Amplex Red is measured here as fluorogenic indicator for the $H_2O_2$ formed. In detail, autotaxin converts the substrate lysophosphatidylcholine (LPC) into phosphocholine and lysophosphatidylic acid (LPA). After this reaction, the phosphocholine is reacted with alkaline phosphatase to give inorganic phosphate and choline. In the next step, choline is oxidised by choline oxidase to give betaine, with formation of $H_2O_2$. $H_2O_2$ reacts with Amplex Red reagent in the presence of peroxidase (horseradish peroxidase) in a 1:1 stoichiometry and forms the highly fluorescent resorufin. The fluorescence is measured in a reaction-dependent kinetic mode in order that fluorescent signals from possible other fluorescent substances which are not involved in the reaction can be corrected out.

Test Procedure 1.5 μl of a standard solution or of the test substances (substances with the name A(n)) in individual concentrations dissolved in 20 mM Hepes pH 7.2 with a maximum of 7.7% of DMSO are pre-incubated together with 10 μl (16 ng) of highly purified recombinant autotaxin in a black microtitre plate provided with 384 wells at 22° C. for 30 min. The reaction is then initiated by addition of 5 μl of L-α-lysophosphatidylcholine (LPC), where the final concentration of LPC is 75 μM. The mixture is incubated at 37° C. for 90 min. After the incubation, Amplex Red reagent, peroxidase (horseradish peroxidase) and choline oxidase is added, and the fluorescence is immediately measured at 612 nm with excitation of 485 nm in a "Tecan Ultra multimode" reader. The activity of autotaxin is calculated indirectly via detection of the $H_2O_2$ formed.

Material:

Microtitre plate: PS microplate, 384 wells, small volume, black Corning, Cat#3677

Protein: recombinant autotaxin (Baculovirale Hi5 Expression)

Substrate: L-α-lysophosphatidylcholine (chicken egg)); Avanti Polar Lipids #830071P Standard: C14 LPA, Avanti Polar Lipids, Cat#857120P Detection reagent: Amplex Red reagent; Invitrogen # A12222; dissolved in 1.923 ml of DMSO peroxidase type VI-A (horseradish) from Sigma # P6782; dissolved in 7.45 ml of test buffer, choline oxidase; Sigma # C5896; dissolved in 2.47 ml of test buffer Detection reagent mix: 1:100 dilution of Amplex Red reagent in test buffer Test buffer: 200 mM Tris HCl, Merck, Cat #1.08219, pH 7.9, 0.1% of BSA, lipid-free, Roche Cat#775835

The following examples relate to medicaments:

EXAMPLE B

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE C

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE D

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE E

Ointment 500 mg of an active ingredient of the formula I are mixed with 99.5 g of Vaseline under aseptic conditions.

EXAMPLE F

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE G

Dragees

Tablets are pressed analogously to Example E and subsequently coated in a conventional manner with a coating of sucrose, potato starch, talc, tragacanth and dye.

EXAMPLE H

Capsules 2 kg of active ingredient of the formula I are introduced into hard gelatine capsules in a conventional manner in such a way that each capsule contains 20 mg of the active ingredient.

EXAMPLE I

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

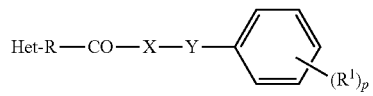

in which $R^1$ denotes H, A, Hal, $OR^3$, $N(R^3)_2$, $N=CR^3N(R^3)_2$, $SR^3$, $NO_2$, CN, $COOR^3$, $CON(R^3)_2$, $NR^3COA$, $NR^3SO_2A$, $SO_2N(R^3)_2$, $S(O)_mA$, $—[C(R^3)_2]_nN(R^3)_2$, $O[C(R^3)_2]_pN(R^3)_2$, $S[C(R^3)_2]_nN(R^3)_2$, $—NR^3[C(R^3)_2]_nN(R^3)_2$, $NHCON(R^3)_2$, $CON(R^3)_2$, $CONR^3[C(R^3)_2]_nN(R^3)_2$ or COA, $R^3$ denotes H or A, X denotes O, NH or $CH_2$, Y denotes $CH_2$, $CH_2O$ or is absent, R denotes

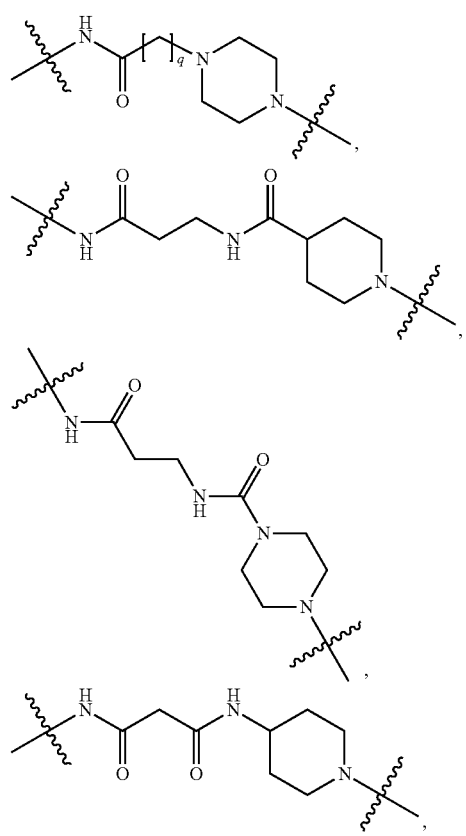

-continued

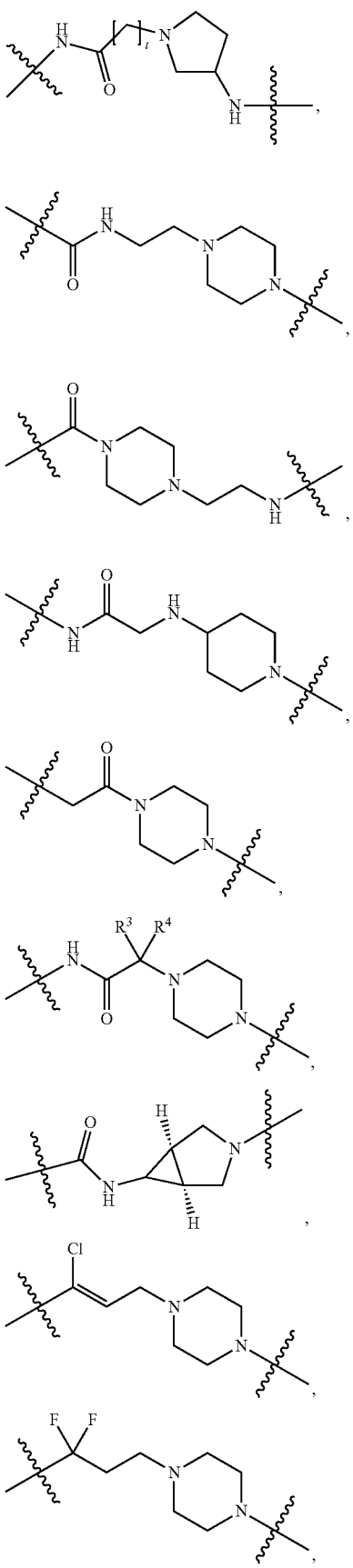

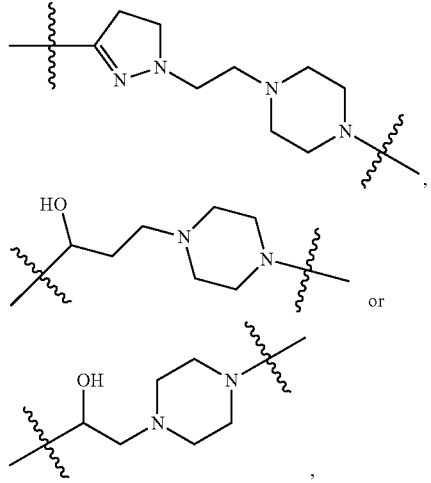

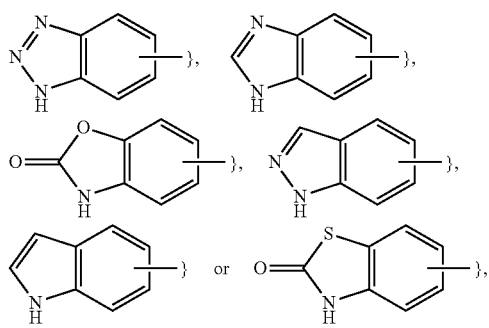

q denotes 2 or 3,
t denotes 1 or 2,
R⁴ denotes H, A or phenyl,
Het denotes

[structures of benzotriazole, benzimidazole, benzoxazolone, indazole, indole, benzothiazolone]

A denotes unbranched or branched alkyl having 1-10 C atoms, in which 1-7H atoms are optionally replaced by OH, F, Cl and/or Br, and/or in which one or two CH₂ groups optionally replaced by O, NH and/or S, or a cyclic alkyl having 3-7 C atoms,
Hal denotes F, Cl, Br or I,
n denotes 0, 1, 2 or 3,
m denotes 0, 1 or 2,
p denotes 0, 1, 2, 3, 4 or 5,
or a pharmaceutically acceptable salt or stereoisomer thereof.

2. A compound according to claim 1, in which
R¹ denotes Hal,
or a pharmaceutically acceptable salt or stereoisomer thereof.

3. A compound according to claim 1, in which
X denotes O or CH₂,
or a pharmaceutically acceptable salt or stereoisomer thereof.

4. A compound according to claim 1, in which
Y denotes CH₂ or CH₂O,
or a pharmaceutically acceptable salt or stereoisomer thereof.

5. A compound according to claim 1, in which
A denotes unbranched or branched alkyl having 1-10 C atoms, in which 1-7H atoms are optionally replaced F and/or Cl, or a pharmaceutically acceptable salt or stereoisomer thereof.

6. A compound according to claim 1, in which
p denotes 1, 2 or 3,
or a pharmaceutically acceptable salt or stereoisomer thereof.

7. A compound according to claim 1, in which
$R^1$ denotes Hal,
X denotes O or $CH_2$,
Y denotes $CH_2$ or $CH_2O$,
A denotes unbranched or branched alkyl having 1-10 C atoms, in which 1-7H atoms are optionally replaced F and/or Cl, and
p denotes 1, 2 or 3,
or a pharmaceutically acceptable salt or stereoisomer thereof.

8. A compound, which is one of the following compounds

| No. | Name and/or structure |
|---|---|
| "11" | 3,5-Dichlorobenzyl 4-{[(2-oxo-2,3-dihydrobenzoxazol-6-yl-carbamoyl)methyl]amino}piperidine-1-carboxylate |
| "13" | 3,5-Dichlorobenzyl 4-[3-hydroxy-3-(2-oxo-2,3-dihydrobenz-oxazol-6-yl)propyl]piperazine-1-carboxylate |
| "15" | 4-Chlorobenzyl 4-[(Z)-3-chloro-3-(2-oxo-2,3-dihydrobenzoxazol-6-yl)allyl]piperazine-1-carboxylate |
| "17" | 4-Chlorobenzyl 4-[3,3-difluoro-3-(2-oxo-2,3-dihydrobenzoxazol-6-yl)propyl]piperazine-1-carboxylate |
| "21" | 3,5-Dichlorobenzyl 4-{2-[3-(2-oxo-2,3-dihydrobenzoxazol-6-yl)-4,5-dihydropyrazol-1-yl]ethyl}piperazine-1-carboxylate |
| "24" | 4-Chlorobenzyl 4-(2-1H-benzotriazol-5-ylacetyl)piperazine-1-carboxylate |
| "32" | 4-Chlorobenzyl 4-[2-(1H-benzotriazol-5-yl-carbamoyl)ethylcarbamoyl]piperidine-1-carboxylate |
| "33" | 4-Chlorobenzyl 4-[2-(1H-benzotriazol-5-ylcarbamoyl)ethyl-carbamoyl]piperazine-1-carboxylate |
| "39" | 4-Chlorobenzyl 4-[2-(1H-benzotriazol-5-ylcarbamoyl)acetyl-amino]piperidine-1-carboxylate |

"A1"

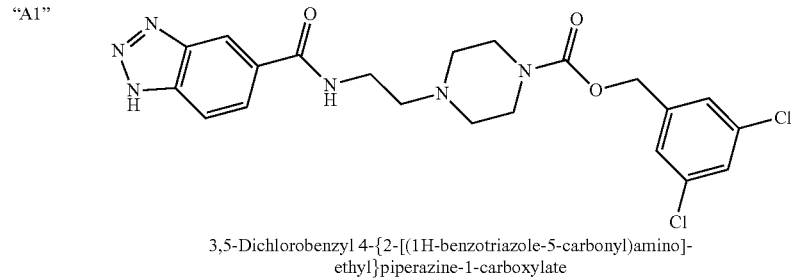

3,5-Dichlorobenzyl 4-{2-[(1H-benzotriazole-5-carbonyl)amino]-ethyl}piperazine-1-carboxylate

"A2"

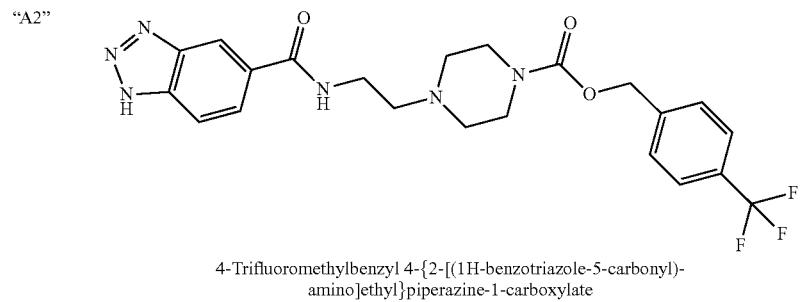

4-Trifluoromethylbenzyl 4-{2-[(1H-benzotriazole-5-carbonyl)-amino]ethyl}piperazine-1-carboxylate

"A3"

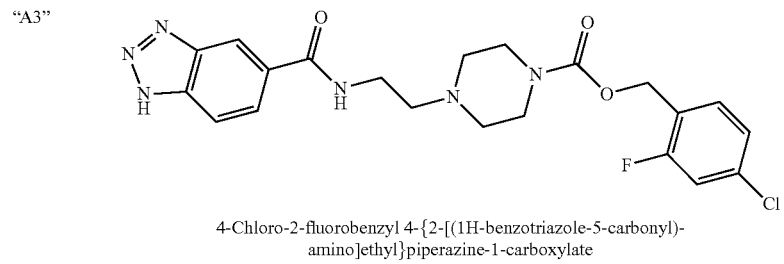

4-Chloro-2-fluorobenzyl 4-{2-[(1H-benzotriazole-5-carbonyl)-amino]ethyl}piperazine-1-carboxylate

| No. | Name and/or structure |
|---|---|
| "A4" | 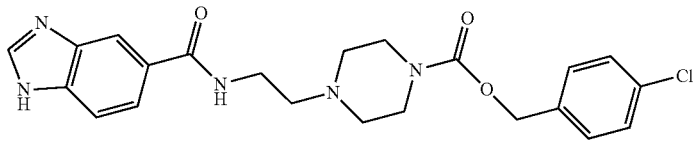 [SMILES: O=C(NCCN1CCN(C(=O)OCc2ccc(Cl)cc2)CC1)c1ccc2[nH]cnc2c1]<br>4-Chlorobenzyl 4-{2-[(1H-benzimidazole-5-carbonyl)amino]-ethyl}piperazine-1-carboxylate |
| "A5" | 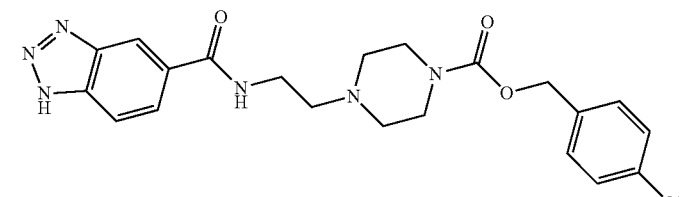<br>4-Chlorobenzyl 4-{2-[(1H-benzotriazole-5-carbonyl)amino]ethyl}-piperazine-1-carboxylate |
| "A6" | 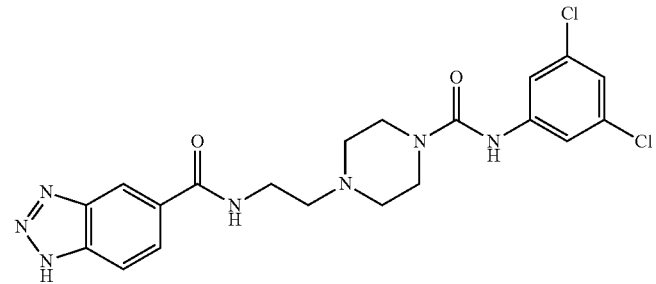 [SMILES: O=C(NCCN1CCN(C(=O)Nc2cc(Cl)cc(Cl)c2)CC1)c1ccc2[nH]nnc2c1]<br>N-{2-[4-(3,5-Dichlorophenylcarbamoyl)piperazin-1-yl]ethyl}-1H-benzotriazole-5-carboxamide |
| "A7" | 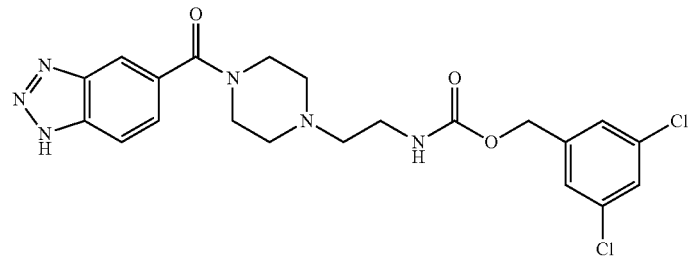 [SMILES: O=C(NCCN1CCN(C(=O)c2ccc3[nH]nnc3c2)CC1)OCc1cc(Cl)cc(Cl)c1]<br>3,5-Dichlorobenzyl {2-[4-(1H-benzotriazole-5-carbonyl)piperazin-1-yl]ethyl}carbamate |
| "A8" | 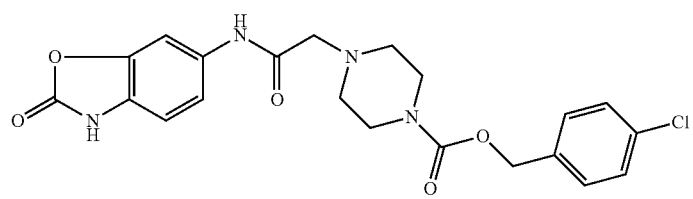 [SMILES: O=C(CN1CCN(C(=O)OCc2ccc(Cl)cc2)CC1)Nc1ccc2[nH]c(=O)oc2c1]<br>4-Chlorobenzyl 4-[(2-oxo-2,3-dihydrobenzoxazol-6-ylcarbamoyl)-methyl]piperazine-1-carboxylate |
| "A9" | 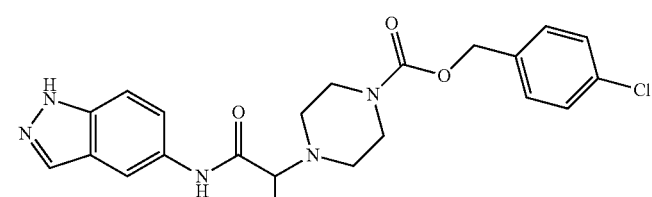<br>4-Chlorobenzyl 4-[1-(1H-indazol-5-ylcarbamoyl)ethyl]piperazine-1-carboxylate |

| No. | Name and/or structure |
|---|---|
| "A10" | 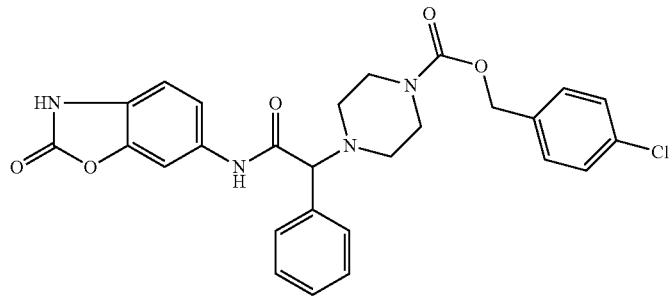 [SMILES: O=C(Nc1ccc2[nH]c(=O)oc2c1)C(c1ccccc1)N1CCN(C(=O)OCc2ccc(Cl)cc2)CC1]
4-Chlorobenzyl 4-[(2-oxo-2,3-dihydrobenzoxazol-6-ylcarbamoyl)-phenylmethyl]piperazine-1-carboxylate |
| "A11" | 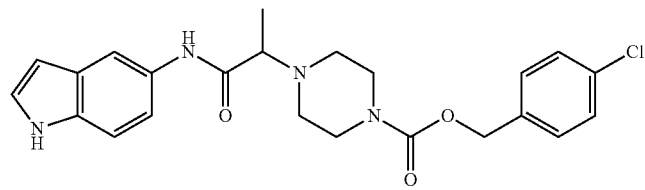 [SMILES: CC(C(=O)Nc1ccc2[nH]ccc2c1)N1CCN(C(=O)OCc2ccc(Cl)cc2)CC1]
4-Chlorobenzyl 4-[1-(1H-indol-5-ylcarbamoyl)ethyl]piperazine-1--carboxylate |
| "A12" | 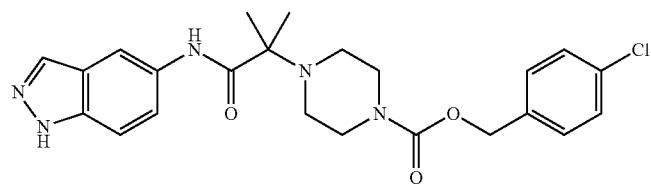 [SMILES: CC(C)(C(=O)Nc1ccc2[nH]ncc2c1)N1CCN(C(=O)OCc2ccc(Cl)cc2)CC1]
4-Chlorobenzyl 4-[1-(1H-indazol-5-ylcarbamoyl)-1-methyl-ethyl]piperazine-1-carboxylate |
| "A13" | 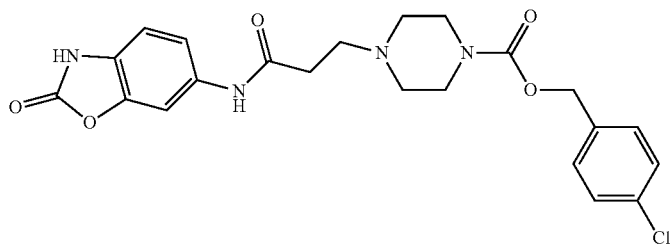 [SMILES: O=C(CCN1CCN(C(=O)OCc2ccc(Cl)cc2)CC1)Nc1ccc2[nH]c(=O)oc2c1]
4-Chlorobenzyl 4-[2-(2-oxo-2,3-dihydrobenzoxazol-6-yl-carbamoyl)ethyl]piperazine-1-carboxylate |
| "A14" | 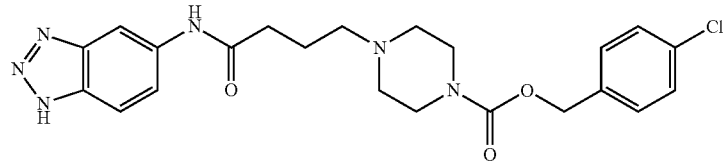 [SMILES: O=C(CCCN1CCN(C(=O)OCc2ccc(Cl)cc2)CC1)Nc1ccc2[nH]nnc2c1]
4-Chlorobenzyl 4-[3-(1H-benzotriazol-5-ylcarbamoyl)propyl]-piperazine-1-carboxylate |

| No. | Name and/or structure |
|---|---|
| "A15" | 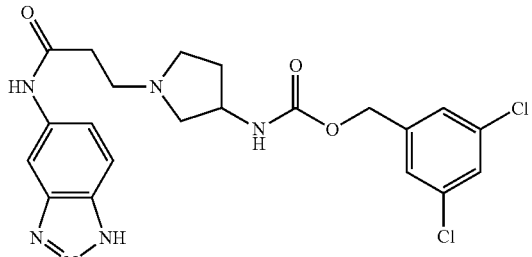<br>3,5-Dichlorobenzyl {1-[2-(1H-benzotriazol-5-ylcarbamoyl)ethyl]-pyrrolidin-3-yl}carbamate |
| "A16" | 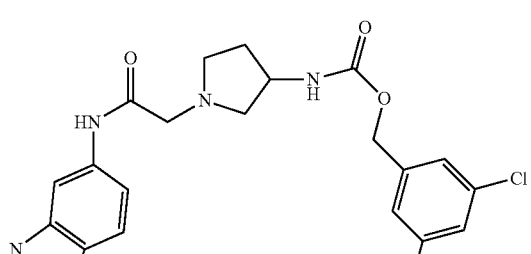<br>3,5-Dichlorobenzyl {1-[(1H-benzotriazol-5-ylcarbamoyl)methyl]-pyrrolidin-3-yl}crbamate |
| "A17" | 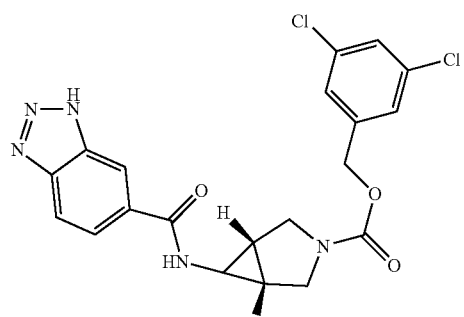<br>3,5-Dichlorobenzyl (1R,5S)-6-[(3H-benzotriazole-5-carbonyl)-amino]-3-azabicyclo[3.1.0]hexane-3-carboxylate |
| "A18" | 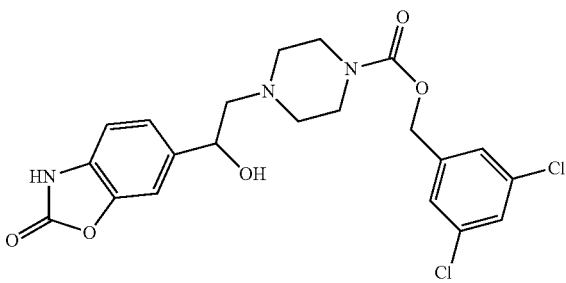 [SMILES: O=C(OCc1cc(Cl)cc(Cl)c1)N1CCN(CC(O)c2ccc3[nH]c(=O)oc3c2)CC1]<br>3,5-Dichlorobenzyl 4-[2-hydroxy-2-(2-oxo-2,3-dihydrobenzoxazol-6-yl)ethyl]piperazine-1-carboxylate | or a pharmaceutically acceptable salt or stereoisomer thereof.

9. A process for preparing a compound of formula I according to claim 1 or a pharmaceutically acceptable salt or stereoisomer thereof, comprising
a) for the preparation of a compound of formula I in which R denotes

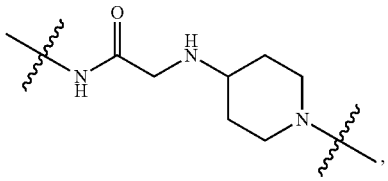 [SMILES: *NC(=O)CNC1CCN(*)CC1]

reacting a compound of formula II

     II in which Het has the meaning indicated for the compound of formula I, and L denotes Cl or Br, with a compound of formula III

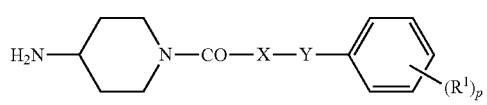     III in which X, Y, $R^1$ and p have the meanings indicated for the compound of formula I,
or
b) for the preparation of a compound of formula I in which R denotes

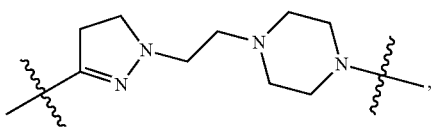 [SMILES: *C1=NN(CCN2CCN(*)CC2)CC1]

reacting a compound of formula IV

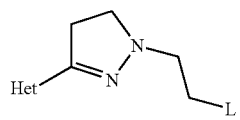     IV in which Het has the meaning indicated for the compound of formula I, and L denotes Cl or Br, with a compound of formula V

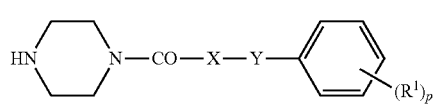     V in which X, Y, $R^1$ and p have the meanings indicated for the compound of formula I,
or
c) for the preparation of a compound of formula I in which R denotes

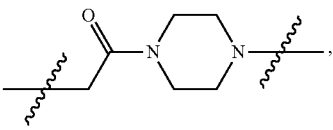 [SMILES: *CC(=O)N1CCN(*)CC1]

reacting a compound of formula VI

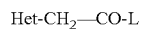     VI in which Het has the meaning indicated for the compound of formula I, and L denotes Cl, Br, I or a free or reactively functionally modified OH group,
with a compound of formula V,
or
d) for the preparation of a compound of formula I in which R denotes

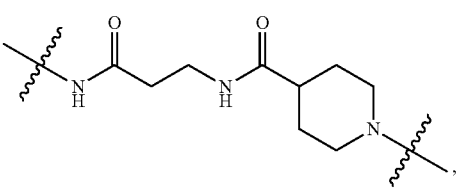 [SMILES: *NC(=O)CCNC(=O)C1CCN(*)CC1]

reacting a compound of formula VII

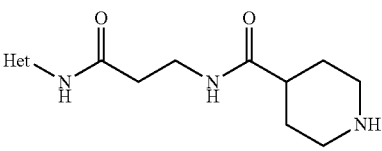     VII in which Het has the meaning indicated for the compound of formula I, with a compound of formula VIII

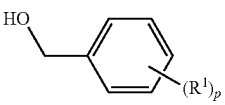     VIII in which $R^1$ and p have the meanings indicated for the compound of formula I,
and a compound selected from the group consisting of carbonyldiimidazole, phosgene, diphosgene, and triphosgene,
or
e) for the preparation of a compound of formula I in which R denotes

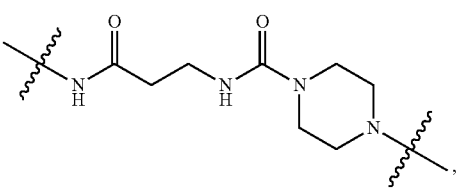 [SMILES: *NC(=O)CCNC(=O)N1CCN(*)CC1]

reacting a compound of formula IX

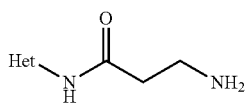

in which Het has the meaning indicated for the compound of formula I,
with a compound of formula V
and a compound selected from the group consisting of carbonyldiimidazole, phosgene, diphosgene, and triphosgene,
or
for the preparation of a compound of formula I in which R denotes

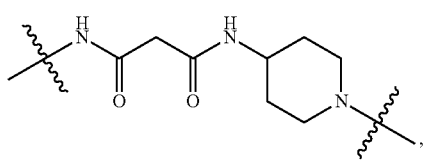 [SMILES: *NC(=O)CC(=O)NC1CCN(*)CC1]

reacting a compound of formula X

Het-NH$_2$     X in which Het has the meaning indicated for the compound of formula I,
with a compound of formula XI

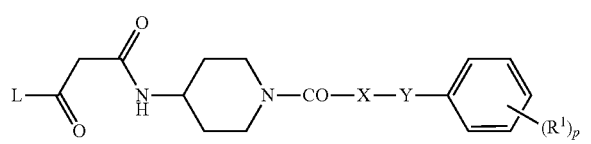

in which X, Y, R$^1$, p have the meanings indicated for the compound of formula I, and L denotes Cl, Br, I or a free or reactively functionally modified OH group,
and/or converting a base or acid compound of formula I into one of its salts.

10. A pharmaceutical composition comprising at least one compound of formula I according to claim 1 or a pharmaceutically acceptable salt or stereoisomer thereof, and one or more pharmaceutically acceptable excipients and/or adjuvants.

11. A method for inhibiting autotaxin, comprising administering to a patient in need thereof a therapeutically effective amount of a compound according to claim 1.

12. A method for inhibiting autotaxin, comprising administering to a patient in need thereof a therapeutically effective amount of a compound according to claim 8.

13. A method for inhibiting autotaxin, comprising administering to a patient in need thereof a therapeutically effective amount of a compound according to claim 7.

14. A method for inhibiting autotaxin, comprising administering to a patient in need thereof a therapeutically effective amount of a compound according to claim 2.

15. A compound, which is

| No. | Name |
|---|---|
| "27" | 6-(2-{4-[3-(4-Chlorophenoxy)propionyl]piperazin-1-yl}-acetyl)-3H-benzoxazol-2-one | or a pharmaceutically acceptable salt or stereoisomer thereof.

16. A method for inhibiting autotaxin, comprising administering to a patient in need thereof a therapeutically effective amount of a compound according to claim 15.

17. A compound according to claim 1, in which R denotes

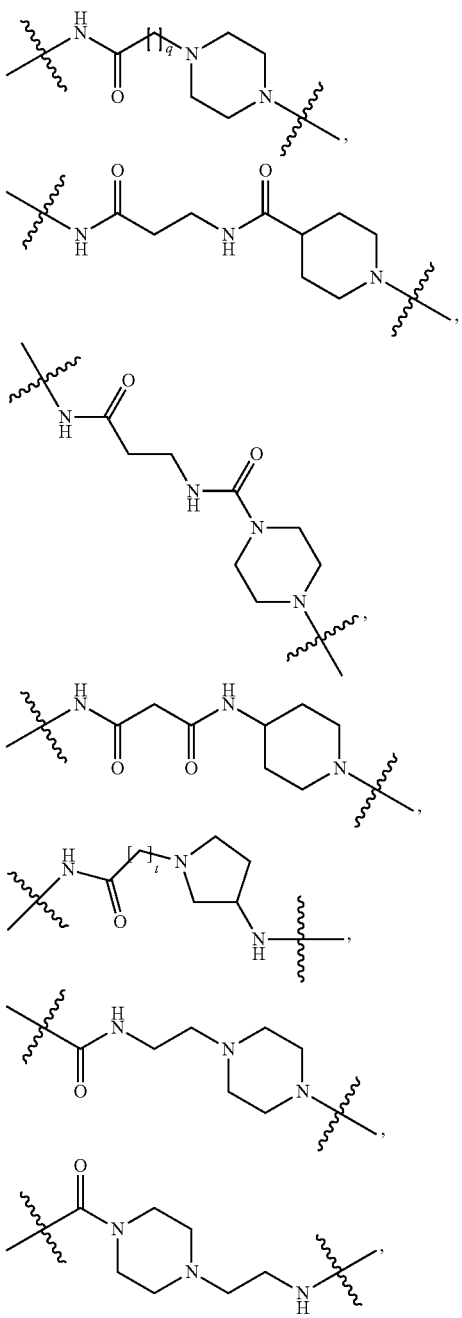

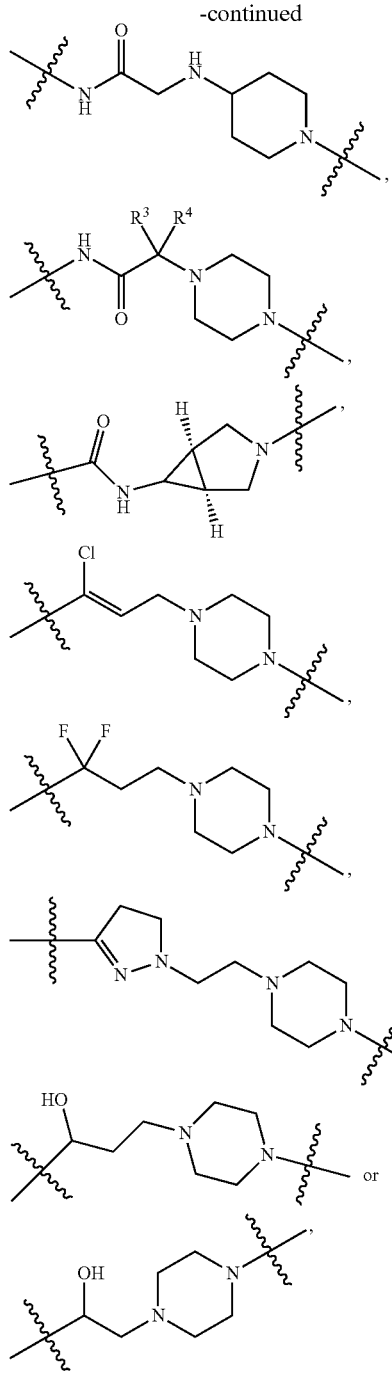
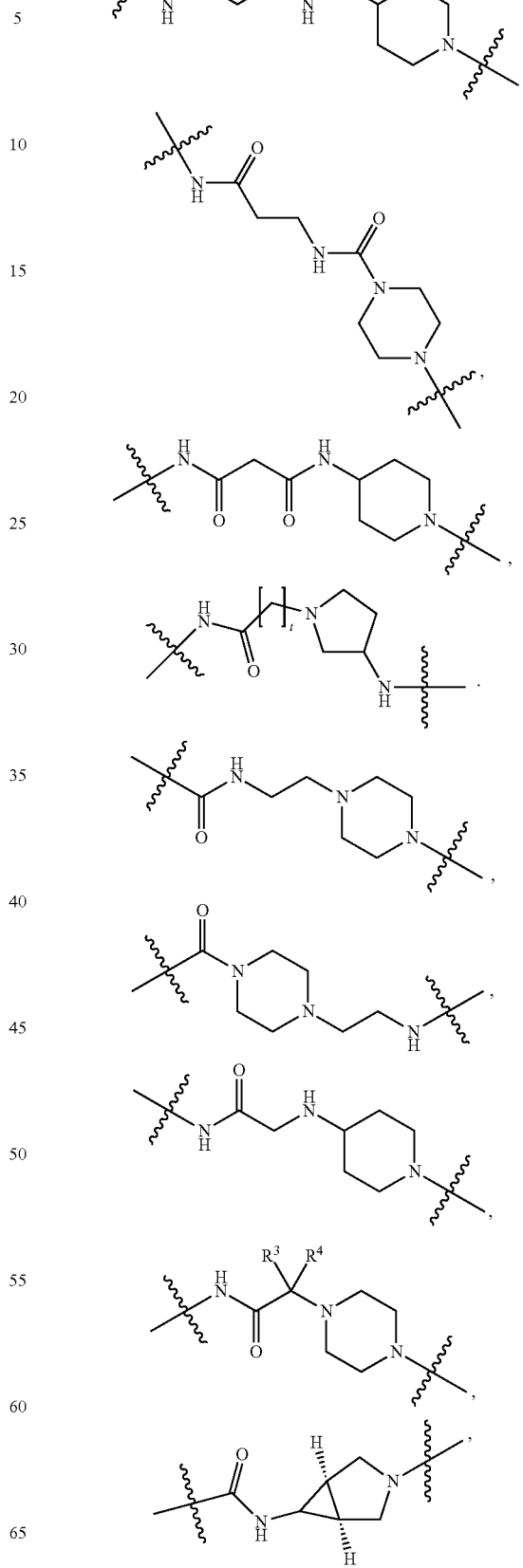
or a pharmaceutically acceptable salt or stereoisomer thereof.
18. A compound according to claim 1, in which R denotes
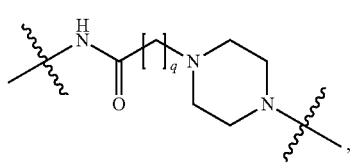

-continued
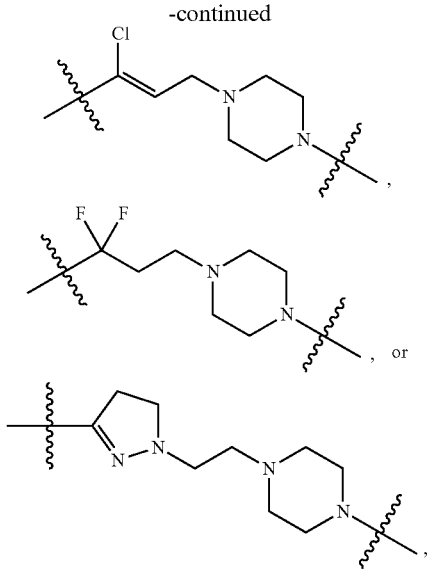, or
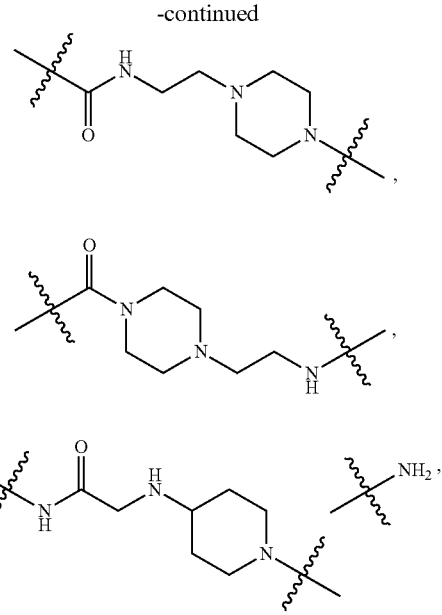,
or a pharmaceutically acceptable salt or stereoisomer thereof.
19. A compound according to claim 1, in which R denotes
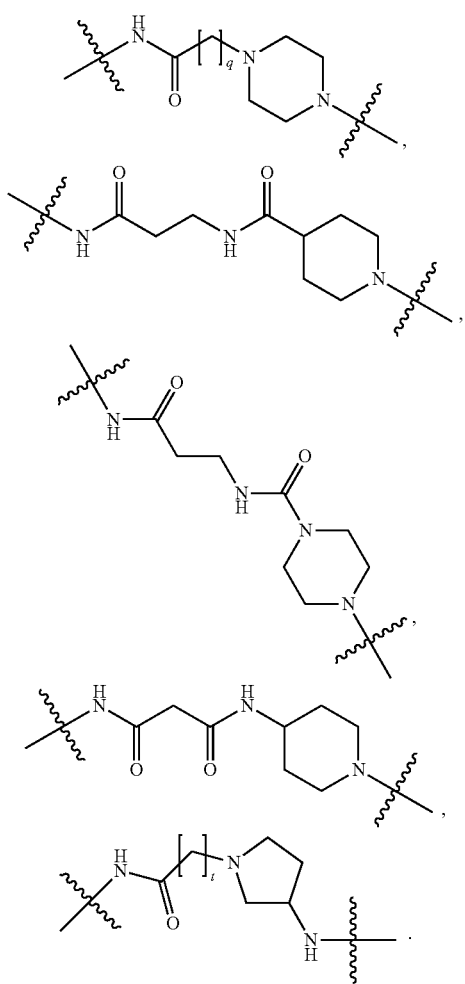
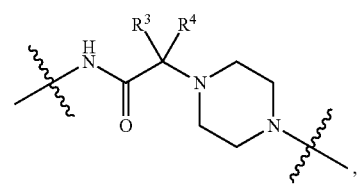
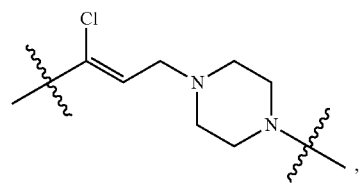
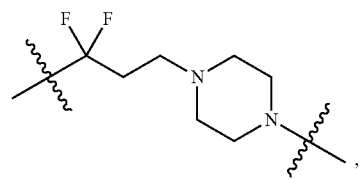
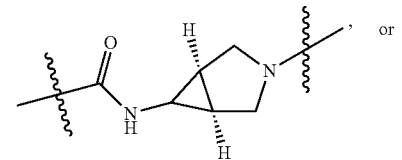, or
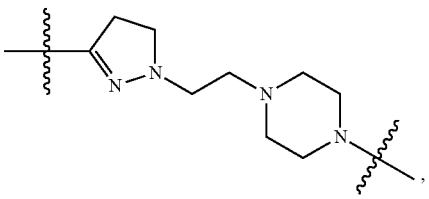,
or a pharmaceutically acceptable salt or stereoisomer thereof.
20. A method for inhibiting autotaxin, comprising administering to a patient in need thereof a therapeutically effective amount of a compound according to claim 19.
* * * * *

UNITED STATES PATENT AND TRADEMARK OFFICE
CERTIFICATE OF CORRECTION

| | |
|---|---|
| PATENT NO. | : 8,841,324 B2 |
| APPLICATION NO. | : 13/259464 |
| DATED | : September 23, 2014 |
| INVENTOR(S) | : Wolfgang Staehle et al. |

It is certified that error appears in the above-identified patent and that said Letters Patent is hereby corrected as shown below:

IN THE CLAIMS:

Column 73, line 17 (Claim 9), reads as follows: -- for the preparation of a compound of formula I in which --.

Should read: -- f) for the preparation of a compound of formula I in which --.

Column 78 (Claim 19): The third compound from the top presents as:

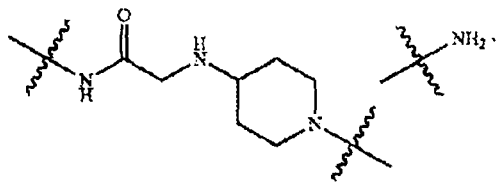

Should present as:

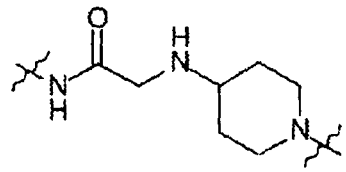

Signed and Sealed this
Second Day of June, 2015

Michelle K. Lee
*Director of the United States Patent and Trademark Office*